(12) United States Patent
Hart et al.

(10) Patent No.: US 6,663,870 B2
(45) Date of Patent: Dec. 16, 2003

(54) METHODS FOR PROMOTING GROWTH OF BONE USING ZVEGF3

(75) Inventors: Charles E. Hart, Woodinville, WA (US); Debra G. Gilbertson, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/823,033

(22) Filed: Mar. 29, 2001

(65) Prior Publication Data

US 2002/0004225 A1 Jan. 10, 2002

Related U.S. Application Data

(63) Continuation-in-part of application No. 09/457,066, filed on Dec. 7, 1999.
(60) Provisional application No. 60/193,723, filed on Mar. 31, 2000, provisional application No. 60/165,255, filed on Nov. 12, 1999, provisional application No. 60/161,653, filed on Oct. 21, 1999, provisional application No. 60/142,576, filed on Jul. 6, 1999, and provisional application No. 60/111,173, filed on Dec. 7, 1998.

(51) Int. Cl.$^7$ .......................... A61K 38/18; C12N 5/02
(52) U.S. Cl. .................. 424/198.1; 530/350; 435/325
(58) Field of Search ........................ 435/325; 530/351

(56) References Cited

U.S. PATENT DOCUMENTS

| | | | |
|---|---|---|---|
| 4,874,746 A | 10/1989 | Antoniades et al. | 514/21 |
| 5,124,316 A | 6/1992 | Antoniades et al. | 514/12 |
| 5,533,836 A | 7/1996 | Moore | 435/240.31 |
| 5,770,228 A | 6/1998 | Edwards et al. | 424/488 |
| 5,863,297 A | 1/1999 | Walter et al. | 623/16 |
| 6,001,352 A | 12/1999 | Boyan et al. | 424/93.7 |
| 6,391,311 B1 * | 5/2002 | Ferrara et al. | |
| 6,455,283 B1 | 9/2002 | Ferrara et al. | 435/69.4 |

FOREIGN PATENT DOCUMENTS

| | | |
|---|---|---|
| EP | 289584 | 5/1993 |
| WO | 91/05802 | 5/1991 |
| WO | 91/18558 | 12/1991 |
| WO | 93/00050 | 1/1993 |
| WO | 93/20859 | 10/1993 |
| WO | 00/04183 | 1/2000 |
| WO | 01/32197 | 5/2001 |

OTHER PUBLICATIONS

S. Vukicevic et al. Induction of nephrogenic mesenchyme by osteogenic protein 1 (bone morphogenetic protein 7). 1996. Proc. Natl. Acad. Sci. USA, 93: 9021–26.*
P. Parnet et al. IL–1Rrp is a novel receptor–like molecule similar to the type 1 interleukin–1 receptor and its homologous T1/ST2 and IL–1R AcP. 1996. J. Biol. Chem., 271(8): 3967–70.*
Midy et al., *Biochem. Biophys. Res. Comm. 199*: 380–386, 1994.
Li et al., *Trends in Biotechnology 19*: 255–265, 2001.
Stephan et al., *J. Periodontol. 71*: 1887–1892, 2000.
Canalis et al., *Principles of Bone Biology* 619–626, 1996.
Nash et al., *Bone 15*: 203–208, 1994.
Howell et al., *J. Periodontol. 68*: 1186–1193, 1997.
Yu et al., *Am. J. Physiol.* 272 (Cell Physiol. 41): C1709–C1716, 1997.

* cited by examiner

*Primary Examiner*—Lorraine Spector
*Assistant Examiner*—Dong Jiang
(74) *Attorney, Agent, or Firm*—Gary E. Parker

(57) ABSTRACT

Methods for promoting growth of bone, ligament, or cartilage in a mammal are disclosed. The methods comprise administering to said mammal a composition comprising a pharmacologically effective amount of a zvegf3 protein in combination with a pharmaceutically acceptable delivery vehicle. Also disclosed are methods for promoting proliferation or differentiation of osteoblasts, osteoclasts, chondrocytes, or bone marrow stem cells comprising culturing the cells in an effective amount of a zvegf3 protein.

13 Claims, 8 Drawing Sheets

Figure 2A:
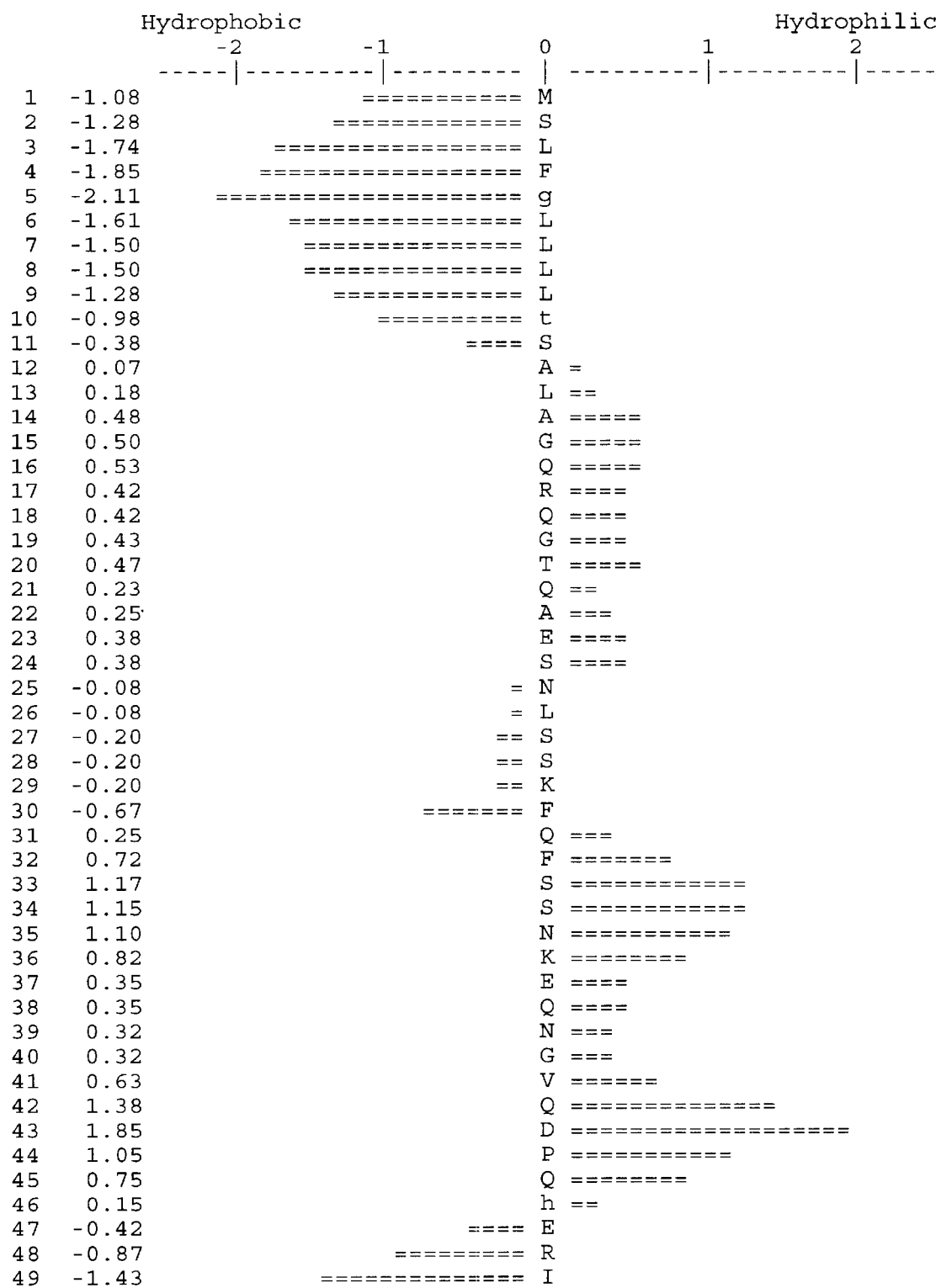

```
MSLFGLLLLTSALAGQRQGTQAESNLSSKFQFSSNKEQNGVQDPQHERIITVSTNGSIHS

MLLLGLLLLTSALAGQRTGTRAESNLSSKLQLSSDKEQNGVQDPRHERVVTISGNGSIHS
         10        20        30        40        50        60

PRFPHTYPRNTVLVWRLVAVEENVWIQLTFDERFGLEDPEDDICKYDFVEVEEPSDGTIL

PKFPHTYPRNMVLVWRLVAVDENVRIQLTFDERFGLEDPEDDICKYDFVEVEEPSDGSVL
         70        80        90       100       110       120

GRWCGSGTVPGKQISKGNQIRIRFVSDEYFPSEPGFCIHYNIVMPQFTEAVSPSVLPPSA

GRWCGSGTVPGKQTSKGNHIRIRFVSDEYFPSEPGFCIHYSIIMPQVTETTSPSVLPPSS
        130       140       150       160       170       180

LPLDLLNNAITAFSTLEDLIRYLEPERWQLDLEDLYRPTWQLLGKAFVFGRKSRVVDLNL

LSLDLLNNAVTAFSTLEELIRYLEPDRWQVDLDSLYKPTWQLLGKAFLYGKKSKVVNLNL
        190       200       210       220       230       240

LTEEVRLYSCTPRNFSVSIREELKRTDTIFWPGCLLVKRCGGNCACCLHNCNECQCVPSK

LKEEVKLYSCTPRNFSVSIREELKRTDTIFWPGCLLVKRCGGNCACCLHNCNECQCVPRK
        250       260       270       280       290       300

VTKKYHEVLQLRPKTGVRGLHKSLTDVALEHHEECDCVCRGSTGG    (SEQ ID NO:2)

VTKKYHEVLQLRPKTGVKGLHKSLTDVALEHHEECDCVCRGNAGG    (SEQ ID NO:43)
        310       320       330       340
```

METHODS FOR PROMOTING GROWTH OF BONE USING ZVEGF3

CROSS-REFERENCE TO RELATED APPLICATIONS

This application is a continuation-in-part of application Ser. No. 09/457,066, filed Dec. 7, 1999, which application is pending, and claims the benefit of provisional applications Ser. No. 60/193,723, filed Mar. 31, 2000, Ser. No. 60/165,255, filed Nov. 12, 1999, Ser. No. 60/161,653, filed Oct. 21, 1999, Ser. No. 60/142,576, filed Jul. 6, 1999, and Ser. No. 60/111,173, filed Dec. 7, 1998.

BACKGROUND OF THE INVENTION

Bone remodeling is the dynamic process by which tissue mass and skeletal architecture are maintained. The process is a balance between bone resorption and bone formation, with two cell types, the osteoclast and osteoblast, thought to be the major players. Osteoblasts synthesize and deposit new bone into cavities that are excavated by osteoclasts. The activities of osteoblasts and osteoclasts are regulated by many factors, systemic and local, including growth factors.

Many of the proteins that influence the proliferation, differentiation, and activity of osteoblasts, osteoclasts, and their precursors also affect these processes in chondrocytes, the cells responsible for cartilage formation (chondrogenesis). These proteins include platelet-derived growth factor (PDGF), insulin-like growth factor (IGF), basic fibroblast growth factor (bFGF), transforming growth factor beta (TGF-β), bone morphogenetic proteins (BMPs), and cartilage-derived growth factor (CDGF).

The exact mode by which PDGF affects the growth of osteoblasts is not yet clearly understood, however, this growth factor is generally believed to play a key role in the regulation of both normal skeletal remodeling and fracture repair. Biologically active PDGF is found as a homodimer or a heterodimer of the component A and B chains. In vitro studies have shown PDGF to be mitogenic for osteoblasts (Abdennagy et al., *Cell Biol. Internat. Rep.* 16(3):235–247, 1992). Mitogenic activity as well as chemotactic activities associated with PDGF have been demonstrated when the growth factor is added to normal osteoblast-like cells (Tuskamota et al., *Biochem. Biophys. Res. Comm.* 175(3): 745–747, 1991) and primary osteoblast cultures (Centrella et al. *Endocrinol.* 125(1):13–19, 1989). Recent studies have demonstrated that the osteoblast produces the AA isoform of PDGF (Zhang et al., *Am. J. Physiol.* 261:c348–c354, 1991).

PDGF has been shown to be useful for promoting the repair of both soft and hard tissues. For example, PDGF has been shown to promote the regeneration of bone and ligament in patients suffering from periodontal disease (Howell et al., *J. Periodontol.* 68:1186–1193, 1997). As disclosed in U.S. Pat. No. 5,533,836, PDGF stimulates the growth of osteoblasts, and this activity is enhanced in the presence of vitamin D. PDGF has also been shown to promote the healing of gastrointestinal ulcers (U.S. Pat. No. 5,234,908) and dermal ulcers (Robson et al., *Lancet* 339:23–25, 1992; Steed et al., *J. Vasc. Surg.* 21:71–81, 1995). The use of PDGF for stimulating chondrocyte proliferation and regenerating cartilage is disclosed in U.S. Pat. No. 6,001,352.

A PDGF homolog known as "zvegf3" was recently identified (U.S. patent application Ser. No. 09/457,066). This protein has also been designated "VEGF-R" (WIPO Publication WO 99/37671). Zvegf3/VEGF-R is a multi-domain protein with significant homology to the PDGF/VEGF family of growth factors. WO 99/37671 discloses that VEGF-R is an angiogenic factor.

Despite the increasing knowledge of the role of growth factors in tissue growth and repair, there remains a need in the art for materials and methods for promoting the growth of bone, ligament, and cartilage. There also remains a need the art for materials and methods for modulating the proliferation and differentiation of cells in vitro and in vivo.

DESCRIPTION OF THE INVENTION

The present invention provides a method for promoting growth of bone, ligament, or cartilage in a mammal comprising administering to said mammal a composition comprising a pharmacologically effective amount of a dimeric protein comprising residues 235–345 of SEQ ID NO:2 or SEQ ID NO:4 and a pharmaceutically acceptable delivery vehicle. Within certain embodiments of the invention the delivery vehicle is powdered bone, tricalcium phosphate, hydroxyapatite, polymethacrylate, a biodegradable polyester, an aqueous polymeric gel, or a fibrin sealant. Within another embodiment of the invention the composition is locally administered at a site of a bony defect, such as a fracture, bone graft site, implant site, or periodontal pocket. Within another embodiment of the invention, the composition is administered systemically. Within a further embodiment of the invention, the zvegf3 protein is covalently linked to a bone-targetting agent. Within a further embodiment of the invention, the composition is locally administered at a joint. The composition may further comprise a protein selected from the group consisting of insulin-like growth factor 1, platelet-derived growth factor, epidermal growth factor, transforming growth factor-alpha, transforming growth factor-beta, a bone morphogenetic protein, parathyroid hormone, osteoprotegerin, a fibroblast growth factor, and a protein comprising residues 258–370 of SEQ ID NO:5 (a zvegf4 protein). Within another embodiment of the invention, the protein is a homodimer. Within a related embodiment, the protein comprises a first polypeptide chain disulfide bonded to a second polypeptide chain, each of the chains consisting of residues X-345 of SEQ ID NO:2, wherein X is an integer from 226 to 235, inclusive.

The invention also provides a method for promoting growth of bone, ligament, or cartilage in a mammal comprising administering to said mammal a composition comprising a pharmacologically effective amount of a dimeric protein comprising a first polypeptide chain disulfide bonded to a second polypeptide chain, each of the chains comprising of residues 235–345 of SEQ ID NO:2 or SEQ ID NO:4, and a pharmaceutically acceptable delivery vehicle. Within certain embodiments, each of the chains consists of residues X-345 of SEQ ID NO:2, wherein X is an integer from 226 to 235, inclusive. Within other embodiments, each of the chains consists of residues X-345 of SEQ ID NO:2, wherein X is an integer from 15 to 20, inclusive.

The invention also provides a method for promoting proliferation or differentiation of cells comprising culturing the cells in an effective amount of a dimeric protein comprising residues 235–345 of SEQ ID NO:2 or SEQ ID NO:4, wherein the cells are osteoblasts, osteoclasts, chondrocytes, or bone marrow stem cells. Within one embodiment the cells are bone marrow stem cells, and the method comprises harvesting the bone marrow stem cells from a patient prior to culturing. Within other embodiments the method further comprises the step of recovering osteoblasts, osteoclasts, or chrodrocytes from the cultured cells. Within additional embodiments the protein comprises a first polypeptide chain disulfide bonded to a second polypeptide chain, each of the chains consisting of residues X-345 of SEQ ID NO:2, wherein X is an integer from 226 to 235, inclusive.

The invention also provides a method for promoting cartilage growth comprising the steps of (a) culturing chondrocytes ex vivo in the presence of a dimeric protein comprising residues 235–345 of SEQ ID NO:2 or SEQ ID NO:4 under conditions wherein the chondrocytes proliferate, and (b) placing the cultured chondrocytes into a mammal where cartilage is to be grown. Within one embodiment the chondrocytes are placed into the mammal in association with a biodegradable matrix having sufficient porosity to permit cell ingrowth. Within a related embodiment the matrix comprises a protein selected from the group consisting of insulin-like growth factor 1, platelet-derived growth factor, epidermal growth factor, transforming growth factor-alpha, transforming growth factor-beta, a bone morphogenetic protein, parathyroid hormone, a fibroblast growth factor, a protein comprising residues 258–370 of SEQ ID NO:5, and a dimeric protein comprising residues 235–345 of SEQ ID NO:2 or SEQ ID NO:4. Within other embodiments the protein comprises a first polypeptide chain disulfide bonded to a second polypeptide chain, each of the chains consisting of residues X-345 of SEQ ID NO:2, wherein X is an integer from 226 to 235, inclusive.

The invention further provides a method for stimulating proliferation of osteoblasts or chondrocytes in a mammal comprising administering to the mammal a composition comprising a pharmacologically effective amount of a dimeric protein comprising residues 235–345 of SEQ ID NO:2 or SEQ ID NO:4 in combination with a pharmaceutically acceptable delivery vehicle. Within certain embodiments of the invention the delivery vehicle is powdered bone, tricalcium phosphate, hydroxyapatite, polymethacrylate, a biodegradable polyester, an aqueous polymeric gel, or a fibrin sealant. Within another embodiment the composition is locally administered at a site of a bony defect, such as a fracture, bone graft site, implant site, or periodontal pocket. Within another embodiment the composition is administered systemically. Within a further embodiment the zvegf3 protein is covalently linked to a bone-targetting agent. Within an additional embodiment the composition is locally administered at a joint. Within other embodiments the composition further comprises a protein selected from the group consisting of insulin-like growth factor 1, platelet-derived growth factor, epidermal growth factor, transforming growth factor-alpha, transforming growth factor-beta, a bone morphogenetic protein, parathyroid hormone, osteoprotegerin, a fibroblast growth factor, and a protein comprising residues 258–370 of SEQ ID NO:5. Within additional embodiments the protein comprises a first polypeptide chain disulfide bonded to a second polypeptide chain, each of the chains consisting of residues X-345 of SEQ ID NO:2, wherein X is an integer from 226 to 235, inclusive.

These and other aspects of the invention will become evident upon reference to the following detailed disclosure and the accompanying drawings.

Within the drawings:

FIG. 1 illustrates an alignment of representative human (SEQ ID NO:2) and mouse (SEQ ID NO:4) zvegf3 amino acid sequences.

Figure 2B:
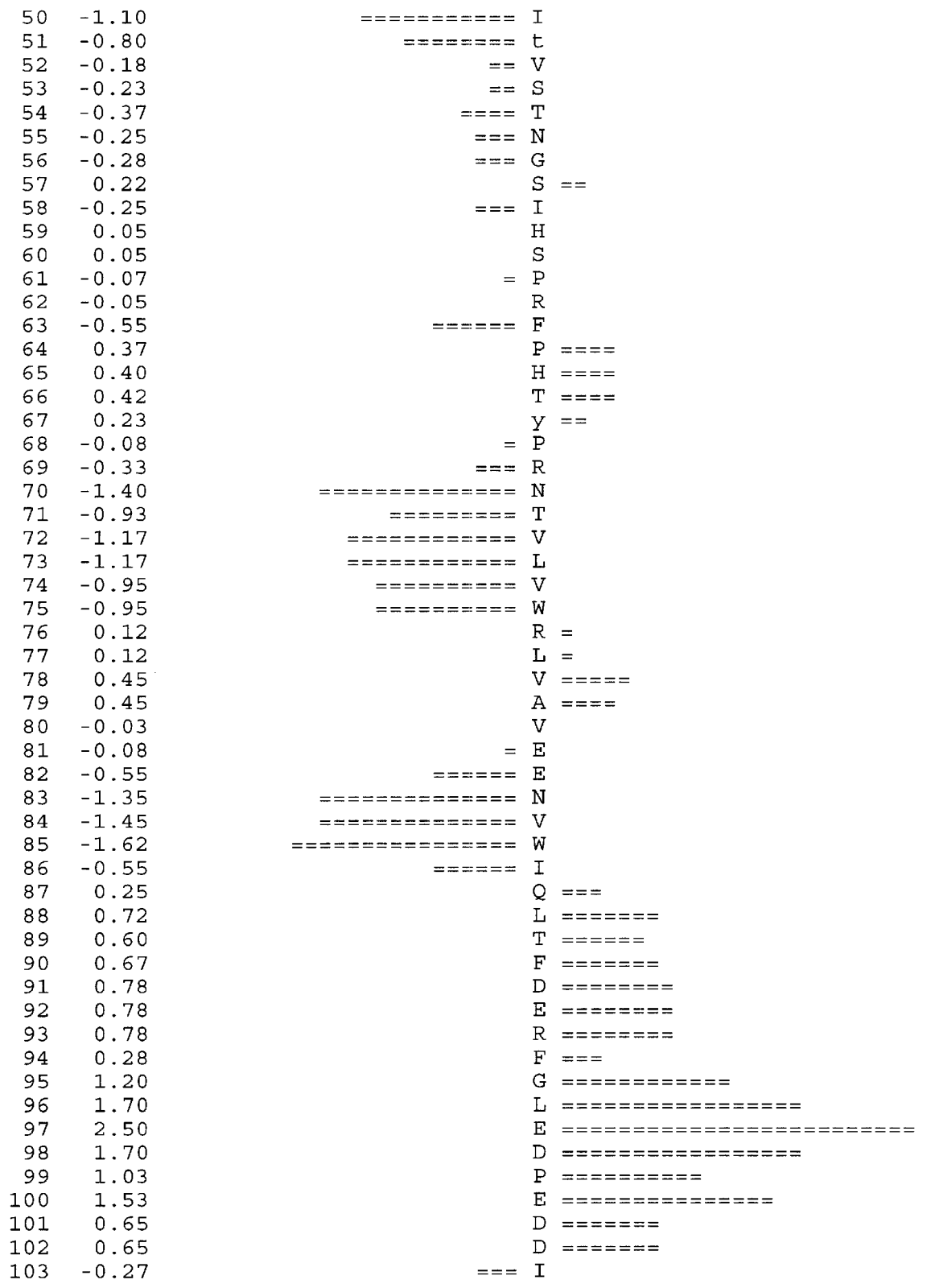
Figure 2C:
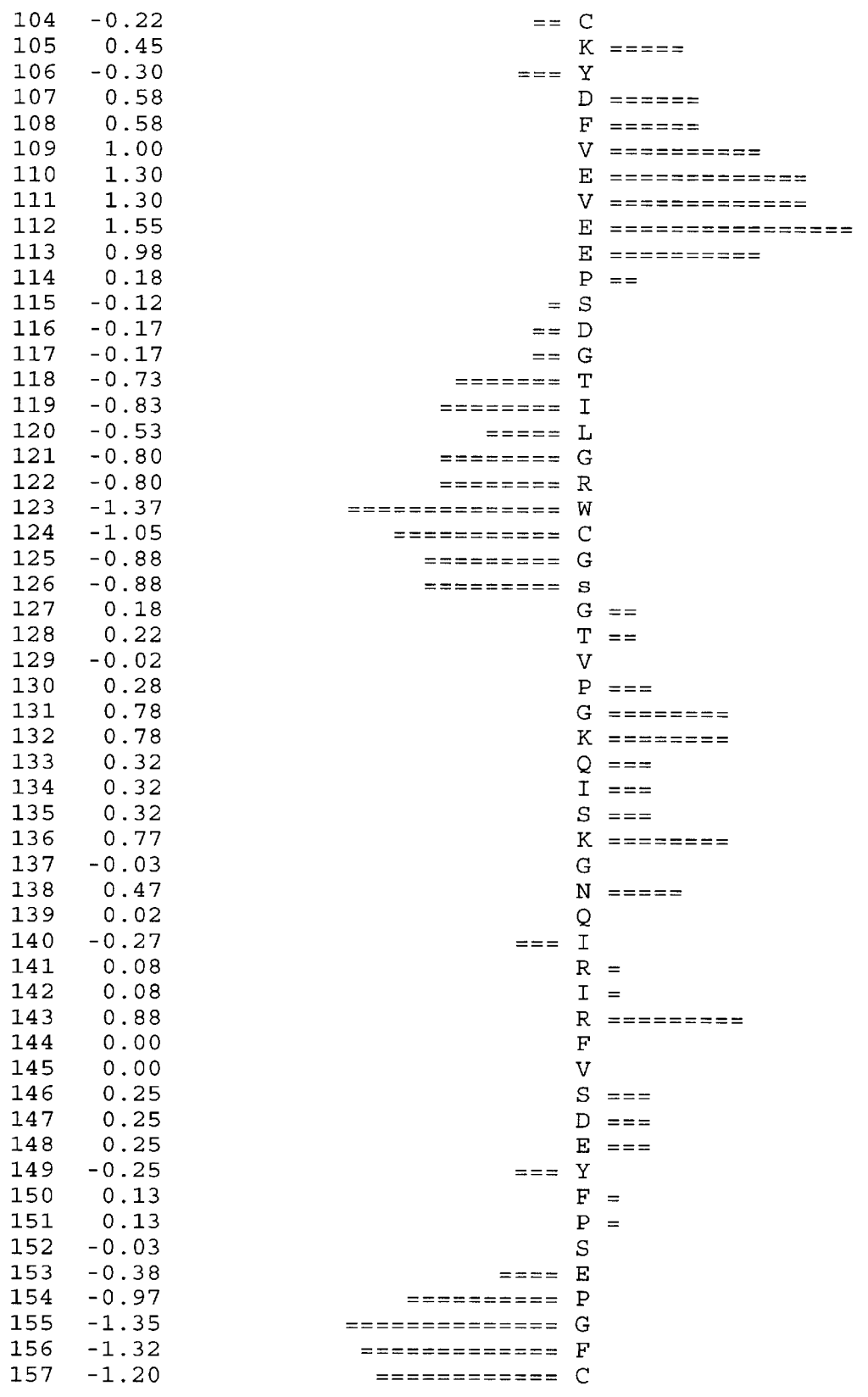
Figure 2D:
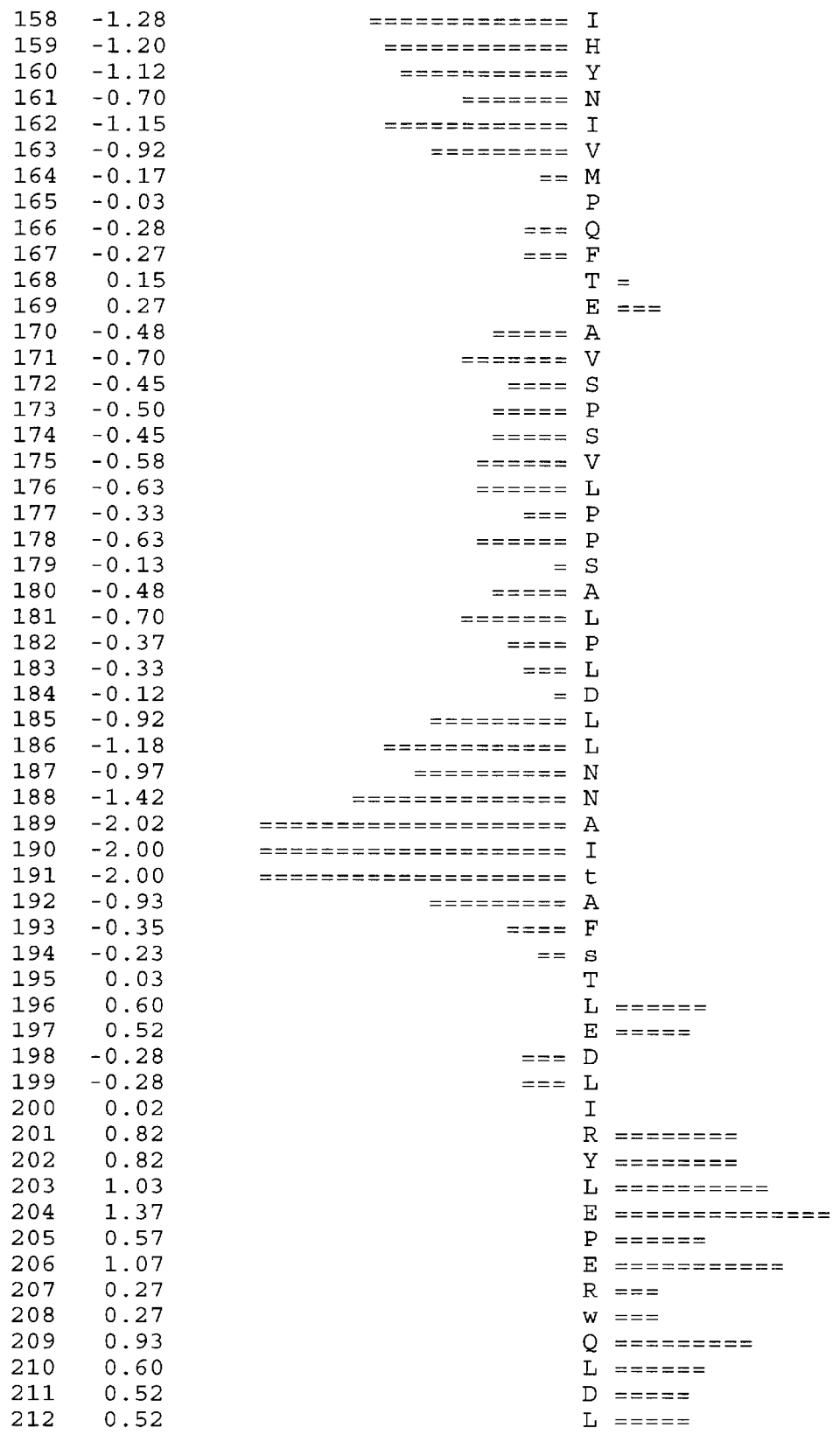
Figure 2E:
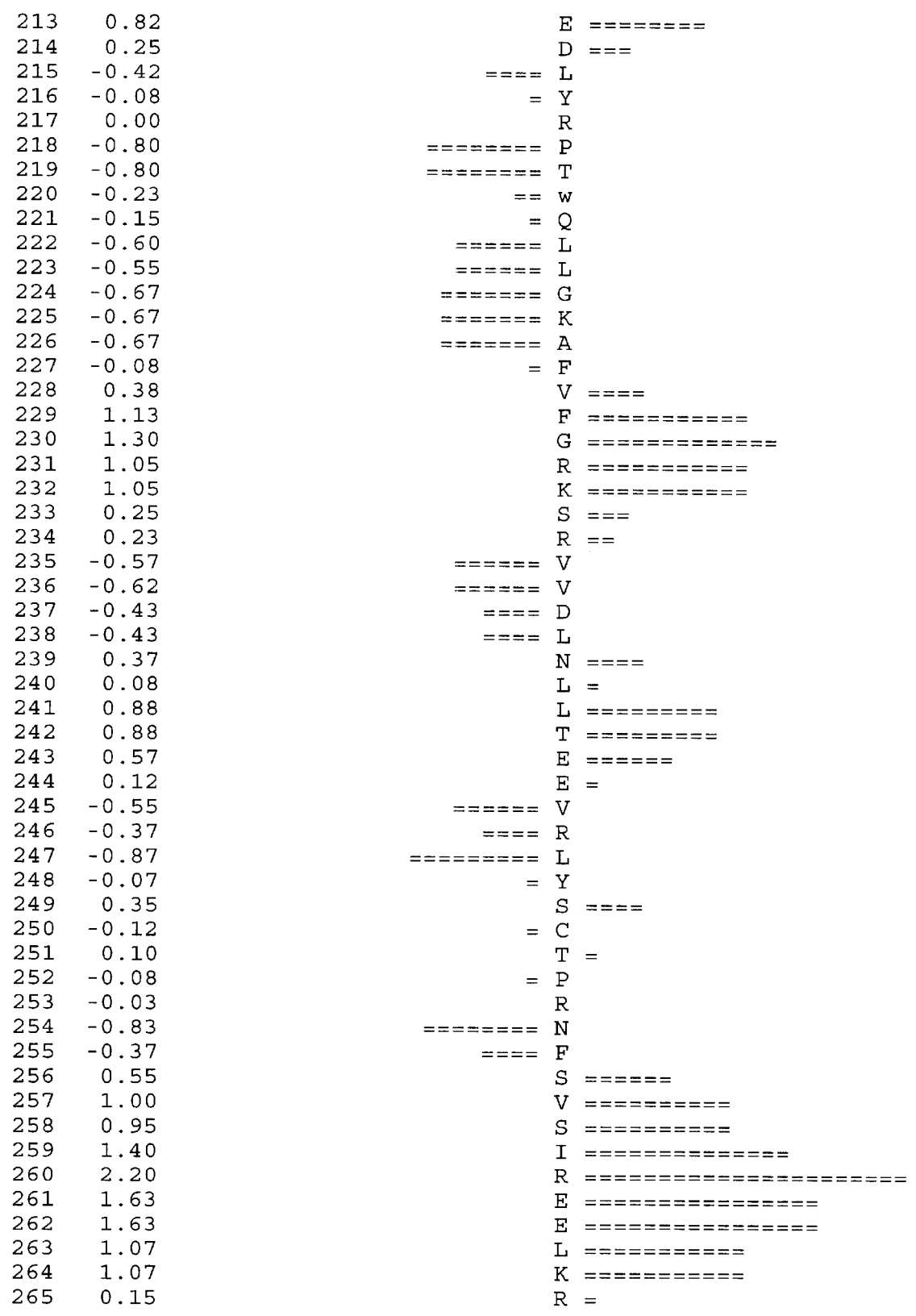
Figure 2F:
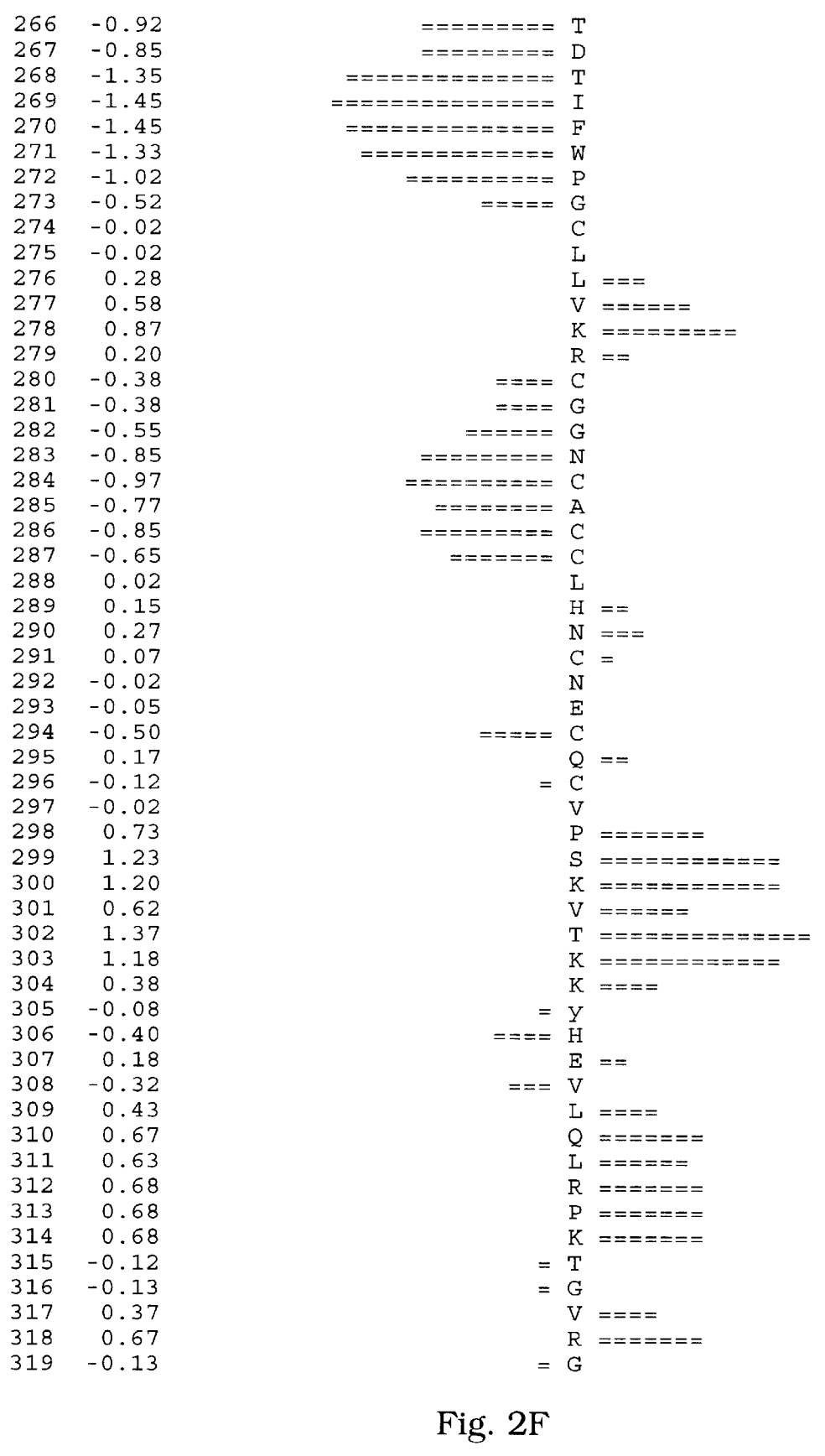
Figure 2G:
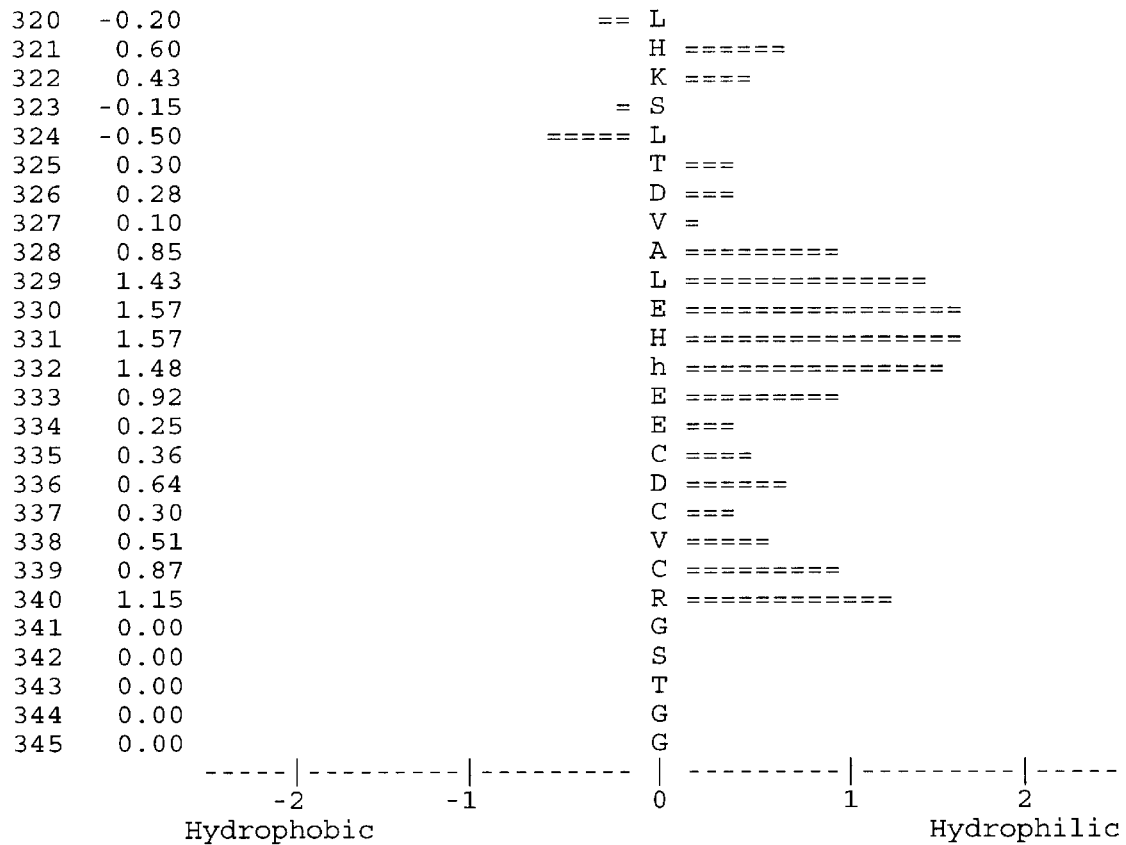

FIGS. 2A–2G are a Hopp/Woods hydrophilicity profile of the amino acid sequence shown in SEQ ID NO:2. The profile is based on a sliding six-residue window. Buried G, S, and T residues and exposed H, Y, and W residues were ignored. These residues are indicated in the figure by lower case letters.

As used herein, the term "bony defect" denotes a defect or void in a bone where restoration of the bone is desirable.

Bony defects may arise from injury, surgery, tumor removal, ulceration, infection, or other causes, and include congenital defects. Examples of bony defects include fractures, voids resulting from tumor removal, and bone loss resulting from periodontal disease.

The terms "locally administered" and "local administration" are used to describe the application of a pharmaceutical agent at the intended site of action. Examples of local administration include, without limitation, injection into a joint space, implantation of a solid or semi-solid matrix, and direct application at a surgical site or wound. Local administration does not preclude the transmission of minor amounts of the agent to other parts of the body, such as by diffusion or circulation.

The term "zvegf3 protein" is used herein to denote proteins comprising the growth factor domain of a zvegf3 polypeptide (e.g., residues 235–345 of human zvegf3 (SEQ ID NO:2) or mouse zvegf3 (SEQ ID NO:4)), wherein said protein is mitogenic for cells expressing cell-surface PDGF α-receptor subunit. Zvegf3 has been found to bind to the αα and αβ isoforms of PDGF receptor. Experimental evidence indicates that biologically active zvegf3 is a dimeric protein. Zvegf3 proteins include homodimers and heterodimers as disclosed below. Using methods known in the art, zvegf3 proteins can be prepared in a variety of forms, including glycosylated or non-glycosylated; pegylated or non-pegylated; with or without an initial methionine residues; and as fusion proteins as disclosed in more detail below.

The present invention provides methods for promoting the growth of bone, connective tissue (including ligament, tendon, and cartilage), and related cell types using zvegf3 proteins. Zvegf3 is a protein that is structurally related to platelet-derived growth factor (PDGF) and the vascular endothelial growth factors (VEGF). The zvegf3 polypeptide chain comprises a growth factor domain and a CUB domain. The growth factor domain is characterized by an arrangement of cysteine residues and beta strands that is characteristic of the "cystine knot" structure of the PDGF family. The CUB domain shows sequence homology to CUB domains in the neuropilins (Takagi et al., *Neuron* 7:295–307, 1991; Soker et al., ibid.), human bone morphogenetic protein-1 (Wozney et al., *Science* 242:1528–1534, 1988), porcine seminal plasma protein and bovine acidic seminal fluid protein (Romero et al., *Nat. Struct. Biol.* 4:783–788, 1997), and *X. laevis* tolloid-like protein (Lin et al., *Dev. Growth Differ.* 39:43–51, 1997).

Structural predictions based on the zvegf3 sequence and its homology to other growth factors suggests that the polypeptide can form homomultimers or heteromultimers having growth factor activity, i.e., modulating one or more of cell proliferation, migration, differentiation, and metabolism. While not wishing to be bound by theory, the similarity of zvegf3 to other members of the PDGF/VEGF family suggests that zvegf3 may also form heteromultimers with other members of the family, including VEGF, VEGF-B, VEGF-C, VEGF-D, zvegf4 (SEQ ID NO:5), PIGF (Maglione et al., *Proc. Natl. Acad. Sci. USA* 88:9267–9271, 1991), PDGF-A (Murray et al., U.S. Pat. No. 4,899,919; Heldin et al., U.S. Pat. No. 5,219,759), or PDGF-B (Chiu et al., *Cell* 37:123–129, 1984; Johnsson et al., *EMBO J.* 3:921–928, 1984).

A representative human zvegf3 polypeptide sequence is shown in SEQ ID NO:2, and a representative mouse zvegf3 polypeptide sequence is shown in SEQ ID NO:4. DNAs encoding these polypeptides are shown in SEQ ID NOS:1 and 3, respectively. An alignment of the mouse and human polypeptide sequences is shown in FIG. 1. Analysis of the amino acid sequence shown in SEQ ID NO:2 indicates that residues 1 to 14 form a secretory peptide. The CUB domain extends from residue 46 to residue 163. A propeptide-like sequence extends from residue 164 to residue 234, and includes two potential cleavage sites at its carboxyl terminus, a dibasic site at residues 231–232 and a target site for furin or a furin-like protease at residues 231–234. The growth factor domain extends from residue 235 to residue 345. Those skilled in the art will recognize that domain boundaries are somewhat imprecise and can be expected to vary by up to ±5 residues from the specified positions. Potential proteolytic cleavage sites occur at residues 232 and 234. Processing of recombinant zvegf3 produced in BHK cells has been found to occur between residues 225 and 226. Signal peptide cleavage is predicted to occur after residue 14 (±3 residues). This analysis suggests that the zvegf3 polypeptide chain may be cleaved to produce a plurality of monomeric species as shown in Table 1. Cleavage after Arg-234 is expected to result in subsequent removal of residues 231–234, with possible conversion of Gly-230 to an amide. Cleavage after Lys-232 is expected to result in subsequent removal of residue 231, again with possible conversion of Gly-230 to an amide. In addition, it may be advantageous to include up to seven residues of the interdomain region at the carboxyl terminus of the CUB domain. The interdomain region can be truncated at its amino terminus by a like amount. See Table 1. Corresponding domains in mouse and other non-human zvegf3s can be determined by those of ordinary skill in the art from sequence alignments.

TABLE 1

| Monomer | Residues (SEQ ID NO:2) |
| --- | --- |
| Cub domain | 15–163 |
|  | 46–163 |
|  | 15–170 |
|  | 46–170 |
| CUB domain + interdomain region | 15–234 |
|  | 46–234 |
|  | 15–229 amide |
|  | 15–230 |
| Cub domain + interdomain region + growth factor domain | 15–345 |
|  | 46–345 |
| Growth factor domain | 235–345 |
|  | 226–345 |
| Growth factor domain + interdomain region | 164–345 |
|  | 171–345 |

Zvegf3 can thus be prepared in a variety of multimeric forms comprising a zvegf3 polypeptide as disclosed above. These zvegf3 polypeptides include $zvegf3_{15-234}$, $zvegf3_{46-234}$, $zvegf3_{15-229}$ amide, $zvegf3_{15-230}$, $zvegf3_{15-345}$, $zvegf3_{46-345}$, and $zvegf3_{235-345}$. Variants and derivatives of these polypeptides can also be prepared as disclosed herein.

Zvegf3 proteins can be prepared as fusion proteins comprising amino- or carboxyl-terminal extensions, such as an amino-terminal methionine residue, an affinity tag, or a targetting polypeptide. For example, a zvegf3 protein can be prepared as a fusion with an affinity tag to facilitate purification. In principle, any peptide or protein for which an antibody or other specific binding agent is available can be used as an affinity tag. Affinity tags include, for example, a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu—Glu affinity tag (Grussenmeyer et al., *Proc. Natl. Acad. Sci. USA* 82:7952–4, 1985), substance P, Flag™ peptide (Hopp et al., *Biotechnology* 6:1204–1210, 1988), streptavidin binding peptide, maltose binding protein (Guan et al., *Gene* 67:21–30, 1987), cellulose binding protein, thioredoxin, ubiquitin, T7 polymerase, or other antigenic epitope or binding domain. Fusion of zvegf3 to, for example, maltose binding protein or glutathione S transferase, can be used to improve yield in bacterial expression systems. In these instances the non-zvegf3 portion of the fusion protein ordinarily will be removed prior to use. Separation of the zvegf3 and non-zvegf3 portions of the fusion protein is facilitated by providing a specific cleavage site between the two portions. Such methods are well known in the art. Zvegf3 can also be fused to a targetting peptide, such as an antibody (including polyclonal antibodies, monoclonal antibodies, antigen-binding fragments thereof such as $F(ab')_2$ and Fab fragments, single chain antibodies, and the like), calcitonin, or other peptidic moiety that binds to bone or connective tissue.

Variations can be made in the zvegf3 amino acid sequences shown in SEQ ID NO:2 and SEQ ID NO:4. Such variations include amino acid substitutions, deletions, and insertions. Amino acid sequence changes are made in zvegf3 polypeptides so as to minimize disruption of higher order structure essential to biological activity. In general, conservative amino acid changes are preferred. Changes in amino acid residues will be made so as not to disrupt the cystine knot and "bow tie" arrangement of loops in the growth factor domain that is characteristic of the protein family. Conserved motifs will also be maintained. The effects of amino acid sequence changes can be predicted by computer modeling as disclosed above or determined by analysis of crystal structure (see, e.g., Lapthorn et al., *Nature* 369:455, 1994). A hydrophobicity profile of SEQ ID NO:2 is shown in FIGS. 2A–2G. Those skilled in the art will recognize that this hydrophobicity will be taken into account when designing alterations in the amino acid sequence of a zvegf3 polypeptide, so as not to disrupt the overall profile. Additional guidance in selecting amino acid subsitutions is provided by the alignment of mouse and human zvegf3 sequences shown in FIG. 1. The amino acid sequence is highly conserved between mouse and human zvegf3s, with an overall amino acid sequence identity of 87%. The secretory peptide, CUB domain, inter-domain, and growth factor domain have 82%, 92%, 79% and 94% amino acid identity, respectively.

It is preferred that the sequence of zvegf3 polypeptide be at least 95% identical to the corresponding region of SEQ ID NO:2 or SEQ ID NO:4. Percent sequence identity is determined by conventional methods. See, for example, Altschul et al., *Bull. Math. Bio.* 48:603–616, 1986, and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.). The percent identity is then calculated as:

$$\frac{\text{Total number of identical matches}}{[\text{length of the longer sequence plus the number of gaps introduced into the longer sequence in order to align the two sequences}]} \times 100$$

Zvegf3 proteins can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–809, 1993; and Chung et al., *Proc. Natl. Acad. Sci. USA* 90:10145–10149, 1993). In a second method, translation is carried out in Xenopus oocytes by microinjection of mutated mRNA and chemically aminoacylated suppressor tRNAs (Turcatti et al., *J. Biol. Chem.* 271:19991–19998, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–7476, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

Essential amino acids in zvegf3 proteins can be identified according to procedures known in the art, such as site-directed mutagenesis or alanine-scanning mutagenesis (Cunningham and Wells, *Science* 244, 1081–1085, 1989; Bass et al., *Proc. Natl. Acad. Sci. USA* 88:4498–4502, 1991). Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Other methods that can be used include phage display (e.g., Lowman et al., *Biochem.* 30:10832–10837, 1991; Ladner et al., U.S. Pat. No. 5,223,409; Huse, WIPO Publication WO 92/06204), region-directed mutagenesis (Derbyshire et al., *Gene* 46:145, 1986; Ner et al., *DNA* 7:127, 1988), and DNA shuffling as disclosed by Stemmer (*Nature* 370:389–391, 1994) and Stemmer (*Proc. Natl. Acad. Sci. USA* 91:10747–10751, 1994). The resultant mutant molecules are tested for mitogenic activity or other properties (e.g., receptor binding) to identify amino acid residues that are critical to the activity of the molecule. Mutagenesis can be combined with high volume or high-throughput screening methods to detect biological activity of zvegf3 variant polypeptides, in particular biological activity in modulating cell proliferation or cell differentiation. For example, mitogenesis assays that measure dye incorporation or $^3$H-thymidine incorporation can be carried out on large numbers of samples.

Using the methods discussed above, one of ordinary skill in the art can identify and/or prepare a variety of polypeptides that are homologous to the zvegf3 polypeptides disclosed above in Table 1 and retain the biological properties of the wild-type protein.

Zvegf3 proteins for use within the present invention, including full-length polypeptides, biologically active fragments, and fusion proteins, can be produced in genetically engineered host cells according to conventional techniques. Suitable host cells are those cell types that can be transformed or transfected with exogenous DNA and grown in culture, and include bacteria, fungal cells, and cultured higher eukaryotic cells (including cultured cells of multicellular organisms). Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, Green and Wiley and Sons, NY, 1993.

In general, a DNA sequence encoding a zvegf3 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zvegf3 polypeptide into the secretory pathway of a host cell, a secretory signal sequence (also known as a leader sequence, prepro sequence or pre sequence) is provided in the expression vector. The secretory signal sequence may be that of zvegf3, or may be derived from another secreted protein (e.g., t-PA; see, U.S. Pat. No. 5,641,655) or synthesized de novo. The secretory signal sequence is operably linked to the zvegf3 DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Expression of zvegf3 polypeptides via a host cell secretory pathway is expected to result in the production of multimeric proteins. As noted above, such multimers include both homomultimers and heteromultimers, the latter including proteins comprising only zvegf3 polypeptides and proteins including zvegf3 and heterologous polypeptides. For example, a heteromultimer comprising a zvegf3 polypeptide and a polypeptide from a related family member (e.g., VEGF, VEGF-B, VEGF-C, VEGF-D, zvegf4, PIGF, PDGF-A, or PDGF-B) can be produced by co-expression of the two polypeptides in a host cell. Sequences encoding these other family members are known. See, for example, Dvorak et al, ibid.; Olofsson et al, ibid.; Hayward et al., ibid.; Joukov et al., ibid.; Oliviero et al., ibid.; Achen et al., ibid.; Maglione et al., ibid.; Heldin et al., U.S. Pat. No. 5,219,759; and Johnsson et al., ibid. If a mixture of proteins results from expression, individual species are isolated by conventional methods. Monomers, dimers, and higher order multimers are separated by, for example, size exclusion chromatography. Heteromultimers can be separated from homomultimers by immunoaffinity chromatography using antibodies specific for individual dimers or by sequential immunoaffinity steps using antibodies specific for individual component polypeptides. See, in general, U.S. Pat. No. 5,094,941. Multimers may also be assembled in vitro upon incubation of component polypeptides under suitable conditions. In general, in vitro assembly will include incubating the protein mixture under denaturing and reducing conditions followed by refolding and reoxidation of the polypeptides to from homodimers and heterodimers. Recovery and assembly of proteins expressed in bacterial cells is disclosed below.

Zvegf3 proteins can be produced in eukaryotic host cells, including fungal cells (e.g., *Saccharomyces cerevisiae, Pichia methanolica,* and *Pichia pastoris*), mammalian cells, plant cells, and insect cells according to conventional methods. See, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; Murray et al., U.S. Pat. No. 4,845,075; Gleeson et al., *J. Gen. Microbiol.* 132:3459–3465, 1986; Cregg, U.S. Pat. No. 4,882,279; Raymond et al., *Yeast* 14:11–23, 1998; McKnight et al., U.S. Pat. No. 4,935,349; Sumino et al., U.S. Pat. No. 5,162,228; Lambowitz, U.S. Pat. No. 4,486,533; Raymond et al., 5,854,039; Raymond, U.S. Pat. Nos. 5,716,808, 5,736,383, and 5,888,768; Levinson et al., U.S. Pat. No. 4,713,339; Hagen et al., U.S. Pat. No. 4,784,950; Palmiter et al., U.S. Pat. No. 4,579,821; Foster et al., U.S. Pat. No. 4,959,318; Mulvihill et al., U.S. Pat. No. 5,648,254; Moore et al., U.S. Pat. No. 5,622,839; Kuestner et al., U.S. Pat. No. 6,008,322; Sinkar et al., *J. Biosci. (Bangalore)* 11:47–58, 1987; Luckow et al., *J. Virol.* 67:4566–4579, 1993; Hill-Perkins and Possee, *J. Gen. Virol.* 71:971–976, 1990; Bonning et al., *J. Gen. Virol.* 75:1551–1556, 1994; and Chazenbalk and Rapoport, *J. Biol. Chem.* 270:1543–1549, 1995. Suitable host strain and cell lines are known in the art and available from public depositories such as the American Type Culture Collection, Manassas, Va., USA. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Expression vectors for use in mammalian cells include pZP-1 and pZP-9, which have been deposited with the American Type Culture Collection, Manassas, Va., USA under accession numbers 98669 and 98668, respectively. Cells, expression vectors, expression kits, and other materials are available from commercial suppliers.

Prokaryotic host cells, including strains of the bacteria *Escherichia coli*, Bacillus and other genera can also be used for production of zvegf3 proteins. Techniques for transforming these hosts and expressing foreign DNA sequences cloned therein are well known in the art (see, e.g., Sambrook et al., ibid.). When expressing a zvegf3 polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the alternative, the protein may be recovered from the cytoplasm in soluble form and isolated without the use of denaturants. The protein is recovered from the cell as an aqueous extract in, for example, phosphate buffered saline. To capture the protein of interest, the extract is applied directly to a chromatographic medium, such as an immobilized antibody or heparin-Sepharose column. Secreted polypeptides can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Zvegf3 polypeptides or fragments thereof can also be prepared through chemical synthesis according to methods known in the art, including exclusive solid phase synthesis, partial solid phase methods, fragment condensation or classical solution synthesis. See, for example, Merrifield, *J. Am. Chem. Soc.* 85:2149, 1963; Stewart et al., *Solid Phase Peptide Synthesis* (2nd edition), Pierce Chemical Co., Rockford, Ill., 1984; Bayer and Rapp, *Chem. Pept. Prot.* 3:3, 1986; and Atherton et al., *Solid Phase Peptide Synthesis: A Practical Approach*, IRL Press, Oxford, 1989.

Covalent complexes can also be made by isolating the desired component polypeptides and combining them in vitro. Covalent complexes that can be prepared in this manner include homodimers of zvegf3 polypeptides, heterodimers of two different zvegf3 polypeptides, and heterodimers of a zvegf3 polypeptide and a polypeptide from another family member of the VEGF/PDGF family of proteins. The two polypeptides are mixed together under denaturing and reducing conditions, followed by renaturation of the proteins by removal of the denaturants. Removal can be done by, for example, dialysis or size exclusion chromatography to provide for buffer exchange. When combining two different polypeptides, the resulting renaturated proteins may form homodimers of the individual components as well as heterodimers of the two polypeptide components. See, Cao et al., *J. Biol. Chem.* 271:3154–3162, 1996.

Zvegf3 proteins are purified by conventional protein purification methods, typically by a combination of chromatographic techniques. See, in general, *Affinity Chromatography: Principles & Methods*, Pharmacia LKB Biotechnology, Uppsala, Sweden, 1988; and Scopes, *Protein Purification: Principles and Practice*, Springer-Verlag, New York, 1994. Proteins comprising a polyhistidine affinity tag (typically about 6 histidine residues) are purified by affinity chromatography on a nickel chelate resin. See, for example, Houchuli et al., *Bio/Technol.* 6: 1321–1325, 1988. Furthermore, the growth factor domain itself binds to nickel resin at pH 7.0–8.0 and 25 mM Na phosphate, 0.25 M NaCl. Bound protein can be eluted with a descending pH gradient down to pH 5.0 or an imidazole gradient. Proteins comprising a glu—glu tag can be purified by immunoaffinity chromatography according to conventional procedures. See, for example, Grussenmeyer et al., ibid. Maltose binding protein fusions are purified on an amylose column according to methods known in the art. As disclosed in more detail below, zvegf3 growth factor domain protein can be purified using a combination of chromatography on a strong cation exchanger followed by hydrophobic interaction chromatography. When the protein is produced in BHK cells, insulin-like growth factor binding protein 4 (IGFBP4) co-purifies with the zvegf3 under these conditions. Further purification can be obtained using reverse-phase HPLC, anion exchange on a quaternary amine strong cation exchanger at low ionic strength and pH from 7.0 to 9.0, or hydrophobic interaction chromatography on a phenyl ether resin. It has also been found that zvegf3 binds to various dye matrices (e.g., BLUE1, BLUE 2, ORANGE 1, ORANGE 3, and RED3 from Lexton Scientific, Signal Hill, Calif.) in PBS at pH 6–8, from which the bound protein can be eluted in 1–2M NaCl in 20 mM boric acid buffer at pH 8.8. Protein eluted from RED3 may be passed over RED2 (Lexton Scientific) to remove remaining contaminants.

Zvegf3 proteins can be used wherever it is desired to stimulate the production of bone and/or connective tissue in both humans and non-human animals. Veterinary uses include use in domestic animals, including livestock and companion animals. Specific applications include, without limitation, fractures, including non-union fractures and fractures in patients with compromised healing, such as diabetics, alcoholics, and the aged; bone grafts; healing bone following radiation-induced osteonecrosis; implants, including joint replacements and dental implants; repair of bony defects arising from surgery, such as cranio-maxilofacial repair following tumor removal, surgical reconstruction following tramatic injury, repair of hereditary or other physical abnormalities, and promotion of bone healing in plastic surgery; treatment of periodontal disease and repair of other dental defects; treatment of bone defects following therapeutic treatment of bone cancers; increase in bone formation during distraction osteogenesis; treatment of joint injuries, including repair of cartilage and ligament; repair of joints that have been afflicted with osteoarthritis; tendon repair and re-attachment; treatment of osteoporosis (including age-related osteoporosis, post-menopausal osteoporosis, glutocorticoid-induced osteoporosis, and disuse osteoporosis) and other conditions characterized by increased bone loss or decreased bone formation; elevation of peak bone mass in pre-menopausal women; and use in the healing of connective tissues associated with dura mater.

For use within the present invention, zvegf3 proteins are formulated for local or systemic (particularly intravenous or subcutaneous) delivery according to conventional methods. In general, pharmaceutical formulations will include a zvegf3 protein in combination with a pharmaceutically acceptable delivery vehicle. Delivery vehicles include biocompatible solid or semi-solid matrices, including powdered bone, ceramics, biodegradable and non-biodegradable synthetic polymers, and natural polymers; tissue adhesives (e.g., fibrin-based); aqueous polymeric gels; aqueous solutions; liposomes; and the like. Exemplary formulations and delivery vehicles are disclosed below. This disclosure is illustrative; those skilled in the art will readily recognize suitable alternatives, including derivatives of the specifically named materials and combinations of materials. Formulations may further include one or more additional growth factors, excipients, preservatives, solubilizers, buffering agents, albumin to prevent protein loss on vial surfaces, etc. Methods of formulation are well known in the art and are disclosed, for example, in *Remington: The Science and Practice of Pharmacy*, Gennaro, ed., Mack Publishing Co., Easton, Pa., 19th ed., 1995. An "effective amount" of a composition is that amount that produces a statistically significant effect, such as a statistically significant increase in the rate of fracture repair, reversal of bone loss in osteoporosis, increase in the rate of healing of a joint injury, increase in the reversal of cartilage defects, increase or acceleration of bone growth into prosthetic devices, improved repair of dental defects, and the like. The exact dose will be determined by the clinician according to accepted standards, taking into account the nature and severity of the condition to be treated, patient traits, etc. Determination of dose is within the level of ordinary skill in the art. Depending upon the route and method of administration, the protein may be administered in a single dose, as a prolonged infusion, or intermittently over an extended period. Intravenous administration will be by bolus injection or infusion over a typical period of one to several hours. Sustained release formulations can be employed. In general, a therapeutically effective amount of zvegf3 is an amount sufficient to produce a clinically significant change in the treated condition, such as a clinically significant reduction in time required for fracture repair, a significant reduction in the volume of a void or other defect, a significant increase in bone density, a significant reduction in morbidity, or a significantly increased histological score.

Zvegf3 will ordinarily be used in a concentration of about 10 to 100 $\mu$g/ml of total volume, although concentrations in the range of 1 $\mu$g/ml to 1000 $\mu$/ml may be used. For local application, such as for the regeneration of bone in a fracture or other bony defect, the protein will be applied in the range of 0.1–100 $\mu$g/cm$^2$ of wound area.

Within the present invention zvegf3 can be used in combination with other growth factors and other therapeutic agents that have a positive effect on the growth of bone or connective tissue. Such growth factors include insulin-like growth factor 1 (IGF-1), PDGF, alpha and beta transforming growth factors (TGF-$\alpha$ and TGF-$\beta$), epidermal growth factor (EGF), bone morphogenetic proteins, leukemia inhibitory factor, fibroblast growth factors, and zvegf4 proteins (e.g., a dimeric protein comprising two disulfide-bonded polypeptide chains, each of said chains comprising residues 258–370 of SEQ ID NO:5). Other therapeutic agents include vitamin D, bisphosphonates, calcitonin, estrogens, parathyroid hormone, osteogenin, NaF, osteoprotegerin, and statins.

Zvegf3 can be delivered as a component of a tissue adhesive. Fibrin-based tissue adhesives are known in the art, and can be prepared from plasma or recombinant sources. Tissue adhesives comprise fibrinogen and factor XII to which thrombin is added immediately before use to activate cross-linking. See, for example, Schwarz et al., U.S. Pat. No. 4,414,976; Stroetmann et al., U.S. Pat. No. 4,427,650; and Rose et al., U.S. Pat. No. 4,928,603. The use of tissue adhesives may be particularly advantageous in the treatment of conditions where connective tissue must be repaired, such as torn ligaments or tendons. Zvegf3 may also be combined with collagen-based adhesives. The collagen may be isolated from natural or recombinant sources.

Solid and semisolid matrices are preferred delivery vehicles for filling non-union fractures, cavities, and other bony defects. These matrices provide a space-filling substitute for the natural bone, and include bone substituting agents such as tricalcium phosphate, hydroxyapatite, combinations of tricalcium phosphate and hydroxyapatite, polymethylmethacrylate, aluminates and other ceramics, and demineralized freeze-dried cortical bone. Solid and semi-solid matrices can also be prepared from a variety of polymeric materials. Semi-solid matrices provide the advantage of maleability such that they can be shaped to provide a precise filling of a bony defect. Matrices may include other active or inert components. Of particular interest are those agents that promote tissue growth or infiltration. Agents that promote bone growth include bone morphogenic proteins (U.S. Pat. No. 4,761,471; PCT Publication WO 90/11366), osteogenin (Sampath et al., *Proc. Natl. Acad. Sci. USA* 84: 7109–7113, 1987), and NaF (Tencer et al., *J. Biomed. Mat. Res.* 23: 571–589, 1989).

Biodegradable, synthetic polymers include polyesters, polyorthoesters, polyanhydrides, polycarbonates, polyfumarates, polyhydroxybutyrate, vinyl polymers, and the like. Specific examples include, without limitation, polylactide, polyglycolide, polylactide/polyglycolide copolymers, polydioxanone, polyglycolide/trimethylene carbonate copolymers, polyacrylic acid, polymethacrylic acid, polyvinyl pyrrolidone, and polyvinyl alcohol. Such materials can be prepared in a variety shapes, including films, plates, pins, rods, screws, blocks, lattices, and the like for attachment to or insertion into bone. See, for example, Walter et al., U.S. Pat. No. 5,863,297; and WIPO publication WO 93/20859. These materials may further include a carrier such as albumin, a polyoxyethylenesorbitan detergent or glutamic acid. In principle, any substance that enhances polymer degradation, creates pores in the matrix or reduces adsorption of the growth factor(s) to the matrix can be used as a carrier. Polyoxyethylenesorbitan detergents that are useful as carriers include polyoxyethylenesorbitan monooleate, polyoxyethylenesorbitan monolaureate, polyoxyethylenesorbitan monopalmitate, polyoxyethylenesorbitan monostearate and polyoxyethylenesorbitan trioleate. Plasticizers can also be included.

In general, a film or device as described herein is applied to the bone at a site of injury. Application is generally by implantation into the bone or attachment to the surface using standard surgical procedures.

Biodegradable polymer films are particularly useful as coatings for prosthetic devices and surgical implants. Such films can, for example, be wrapped around the outer surfaces of surgical screws, rods, pins, plates and the like, or can themselves be rolled or otherwise formed into a variety of shapes. Implantable devices of this type are routinely used in orthopedic surgery. Films can also be used to coat bone filling materials, such as hydroxyapatite blocks, demineralized bone matrix plugs, collagen matrices, and the like.

As used herein the term "copolymer" includes any polymer containing two or more types of monomer unit. Copolymers can be classified in four types as shown in the following chart, wherein "A" and "B" denote the component monomer units:

Random: -A-B-A-A-B-A-B-B-B-A-A-B-
Alternating: -A-B-A-B-A-B-A-B-A-B-A-B-
Block: -A-A-A-A-A-B-B-B-B-B-B-A-A-

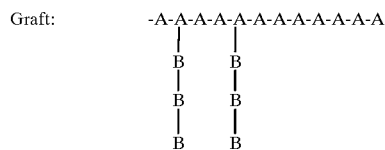

Degradation of the matrix and consequent release of growth factors therefrom can be modulated by adjusting such parameters as molecular weight, copolymer structure, copolymer ratio, matrix thickness, and porosity, and by including a carrier as disclosed above. PLA/PGA films, for example, are generally formulated to provide a ratio of PLA:PGA between 75:25 and 25:75, more commonly between 65:35 and 35:65. In general, an implant will be prepared using a copolymer having a molecular weight between 10,000 and 200,000 Daltons. In general, lower molecular weight copolymers will degrade more rapidly than higher molecular weight formulations; random copolymers are less crystalline and therefore degrade more quickly than other types of copolymers; and polymers of enantiomeric lactides are crystalline and therefore more resistant to degradation than their racemic counterparts.

Polymer matrices are prepared according to procedures known in the art. See, for example, Loomis et al., U.S. Pat. No. 4,902,515; Gilding and Reed, *Polymer* 20: 1459–1464, 1979; and Boswell et al., U.S. Pat. No. 3,773,919. For example, PLA/PGA copolymer implants are produced by combining the desired amount of PLA/PGA copolymer granules in a suitable solvent (e.g., chloroform or methylene chloride), pouring the resulting solution into a mold, and completely evaporating the solvent. In the alternative, PLA/PGA implants can be produced by compression molding, extrusion, or other known methods. To load the matrix, zvegf3 and a carrier are applied as powders or liquid solutions. For example, lyophilized zvegf3 and albumin may be uniformly dispersed over one surface of polymer film, and the film folded over. By repeated this process, a multi-layered "sandwich" of polymer and growth factor can be constructed. In the alternative, the proteins can be applied as aqueous solutions (e.g., in phosphate buffered saline or 0.1 M acetic acid), which are allowed to dry. Porous implants can be soaked in a solution of zvegf3 (optionally containing other components), and the liquid evaporated. Zvegf3 can be worked into a maleable polymeric matrix after which the matrix is formed into the desired shape and cured at elevated temperature (e.g., 60–65° C.). Porous implants can be prepared by curing the matrix under vacuum.

Zvegf3 can also be delivered in combination with a biodegradable sponge, for example a gelatin, collagen, cellulose, or chitin sponge. Such sponges are known in the art. See, for example, Correll, U.S. Pat. No. 2,465,357; Miyata et al., U.S. Pat. No. 4,271,070; and Munck et al., WO 90/13320. A solution of zvegf3 and, optionally, one or more additional therapeutic agents is injected into the sponge, and the sponge is air-dried at a temperature 6f 30–100° C. for a time sufficient to reduce the water content to below 50%, preferably below 10%.

Gels can also be used as delivery vehicles. The use of aqueous, polymeric gels for the delivery of growth factors is disclosed by, for example, Finkenaur et al., U.S. Pat. No. 5,427,778; Edwards et al., U.S. Pat. No. 5,770,228; and Finkenaur et al., U.S. Pat. No. 4,717,717; and Cini et al., U.S. Pat. No. 5,457,093. Gels comprise biocompatible, water soluble or water swellable polymers that form viscous solutions in water. Such polymers include, without limitation, polysaccharides, including methyl cellulose, hydroxypropyl cellulose, hydroxypropylmethyl cellulose, hydroxyethyl cellulose, dextrans, starch, chitosan, and alginic acid; glycosaminoglycans, including hyaluronic acid, chondroitin, chondroitin sulfates, heparin, and heparan sulfate; proteins, including collagen, gelatin, and fibronectin; and acrylamides, including polyacrylamide and polymethacrylamide. Gels are generally prepared with a viscosity of from 200 cps to 100,000 cps, more commonly about 1000 cps to 30,000 cps at room temperature, the latter range corresponding to about 0.25–10% hydroxyethyl cellulose in water. Higher viscosity gels are known in the art (e.g., Finkenaur et al., U.S. Pat. No. 5,427,778). Viscosity can be adjusted by varying the concentration and/or length of the component polymer(s). Gels are prepared by combining the polymer with a suitable buffer, such as a low ionic strength citrate, phosphate, or acetate buffer at neutral or slightly acidic pH. A preservative (antimicrobial agent) such as methyl paraben, propyl paraben, benzyl alcohol, or the like, will generally be included. Following thorough mixing, the solution is sterilized by suitable means (e.g., autoclaving). The mixture is cooled, and filter-sterilized zvegf3 is added.

Alternative means for local delivery of zvegf3 include osmotic minipumps (e.g., ALZET® minipumps; Alza Corporation, Mountain View, Calif.); electrically charged dextran beads as disclosed in Bao et al. (WO 92/03125); collagen-based delivery systems, such as disclosed in Ksander et al. (*Ann. Surg.* 211:288–294, 1990); and alginate-based systems as disclosed in Edelman et al. (*Biomaterials,* 12:619–626, 1991). Other methods known in the art for sustained local delivery in bone include porous coated metal protheses that can be impregnated with a therapeutic agent and solid plastic rods with therapeutic compositions incorporated within them.

Zvegf3 can be further used to treat osteoporosis by administering a therapeutically effective amount of zvegf3 to an individual. Zvegf3 proteins can be tested in intact animals using an in vivo dosing assay. Prototypical dosing may be accomplished by subcutaneous, intraperitoneal or oral administration, and may be performed by injection, sustained release or other delivery techniques. The time period for administration of zvegf3 may vary (for instance, 28 days as well as 35 days may be appropriate).

Delivery of systemically adminstered compositions of the present invention may be enhanced by conjugating zvegf3 to a targeting molecule. A "targeting molecule" is a molecule that binds to the tissue of interest. For example, bone-targeting molecules include tetracyclines, calcein, bisphosphonates, polyaspartic acid, polyglutamic acid, aminophosphosugars, peptides known to be associated with the mineral phase of bone (e.g., osteonectin, bone sialoprotein, and osteopontin), bone-specific antibodies, proteins with bone mineral or bone cell binding domains (e.g., calcitonin), and the like. See, for example, the disclosures of Bentz et al., EP 512,844; Murakami et al., EP 341,961; and Brinkley, *Bioconjugate Chem.* 3:2–13, 1992. Conjugation will ordinarily be achieved through a covalent linkage, the precise nature of which will be determined by the targetting molecule and the linking site on the zvegf3 polypeptide. Typically, a non-peptidic agent is modified by the addition of a linker that allows conjugation to zvegf3 through its amino acid side chains, carbohydrate chains, or reactive groups introduced on zvegf3 by chemical modification. For example, a drug may be attached through the ε-amino group of a lysine residue, through a free α-amino group, by disulfide exchange to a cysteine residue, or by oxidation of the 1,2-diols in a carbohydrate chain with periodic acid to allow attachment of drugs containing various nucleophiles through a Schiff-base linkage. See, for example, Ali et al., U.S. Pat. No. 4,256,833. Protein modifying agents include amine-reactive reagents (e.g., reactive esters, isothiocyantates, aldehydes, and sulfonyl halides), thiol-reactive reagents (e.g., haloacetyl derivatives and maleimides), and carboxylic acid- and aldehyde-reactive reagents. Zvegf3 polypeptides can be covalently joined to peptidic agents through the use of bifunctional cross-linking reagents. Heterobifunctional reagents are more commonly used and permit the controlled coupling of two different proteins through the use of two different reactive moieties (e.g., amine-reactive plus thiol, iodoacetamide, or maleimide). The use of such linking agents is well known in the art. See, for example, Brinkley (ibid.) and Rodwell et al., U.S. Pat. No. 4,671,958. Peptidic linkers can also be employed. In the alternative, a zvegf3 polypeptide can be linked to a peptidic moiety through preparation of a fusion polypeptide.

Zvegf3 can be implanted in a mammalian body so that the zvegf3 is in contact with osteoblasts such that osteoblast proliferation occurs and bone growth is stimulated. For example, zvegf3 can be placed in a matrix in association with a bone morphogenic protein (BMP). The BMP induces the migration of mesenchymal osteoblast precursors to the site and further induces differentiation of the mesenchymal cells into osteoblasts. Zvegf3 will then stimulate the further proliferation of the osteoblasts. A suitable matrix is made up of particles of porous materials. The pores must be of a dimension to permit progenitor cell migration and subsequent differentiation and proliferation, generally in the range of 70–850 µm, commonly from 150 µm to 420 µm. The matrix containing the zvegf3 can be molded into a shape encompassing a bone defect. Examples of matrix materials are particulate, demineralized, guanidine extracted, species-specific bone. Other potentially useful matrix materials include collagen, homopolymers and copolymers of glycolic acid and lactic acid, hydroxyapatite, tricalcium phosphate and other calcium phosphates. Zvegf3 can be applied into a matrix at a sufficient concentration to promote the proliferation of osteoblasts, preferably at a concentration of at least 1 µg/ml of matrix. A solution of zvegf3 can also be injected directly into the site of a bone fracture to expedite healing of the fracture. Examples of BMPs and the use of matrices to produce are disclosed in PCT application publication number WO 92/07073, publication No. WO 91/05802,U.S. Pat. No. 5,645,591 and U.S. Pat. No. 5,108,753.

As stated above, it has also been determined that zvegf3 can be used to promote the production of cartilage through its ability to stimulate the proliferation of chondrocytes. Zvegf3 can be injected directly into the site where cartilage is to be grown. For example, zvegf3 can be injected directly in joints which have been afflicted with osteoarthritis or other injured joints in which the cartilage has been worn down or damaged by trauma. In the alternative, zvegf3 can be delivered in a suitable solid or semi-solid matrix as disclosed above.

Cartilage can also be grown by first removing chondrocytes from a patient and culturing them in the presence of zvegf3 so that they proliferate. Chondrocytes are cultured for from several hours to a day or longer according to conventional methods in a culture medium (e.g., DMEM supplemented with 10% patient's serum) containing from about 0.01 µg/ml to about 100 µg/ml zvegf3. The proliferated chondrocytes are reimplanted into the patient where cartilage needs to be produced. The proliferated chondrocytes can be delivered in a porous matrix having sufficient porosity to permit cell ingrowth as generally disclosed above. Additional zvegf3 can be included in the matrix to promote further chondrocyte proliferation after implantation. See, in general, Walter et al., U.S. Pat. No. 5,863,297 and Boyan et al., U.S. Pat. No. 6,001,352.

Within another embodiment, the present invention provides methods for stimulating the growth and/or differentiation of bone-forming and cartilage-forming cells, or their precursors, in vitro. Using these methods, cells can be harvested from a patient, expanded ex vivo, and returned to the patient as generally disclosed above. Of particular interest is the growth and/or differentiation of bone marrow cells, which can be cultured in the presence of differentiation-stimulating agents to develop into, inter alia, osteoblasts, osteoclasts, and chondrocytes. Identification of differentiated cells within a primary culture is primarily phenotypic. For example, the phenotypic markers for osteoblasts include expression of alkaline phosphatase (Manduca et al., *J. Bone*

*Min. Res.* 8:281, 1993), type 1 collagen synthesis (Kurihara et al., *Endocrinol.* 118(3):940–947, 1986), production of osteocalcin (Yoon et al., *Biochem.* 27:8521–8526, 1988) and responsiveness to parathyroid hormone (Aubin et al., *J. Cell Biol.*, 92:452–461, 1982). Osteoblast cells are typically cultured at 37° C. in 5% $CO_2$ in a growth medium that includes a carbon source, a nitrogen source, essential amino acids, vitamins, minerals and growth factors generally supplied by fetal calf serum. A variety of suitable media are known in the art. Zvegf3 polypeptides are added to tissue culture media for these cell types at a concentration of about 10 pg/mil to about 1000 ng/ml. Those skilled in the art will recognize that zvegf3 proteins can be advantageously combined with other growth factors in culture media.

Bony defects or connective tissue injuries may also be repaired using a gene therapy approach wherein a polynucleotide encoding zvegf3 is administered to a patient. Gene delivery systems useful in this regard include adenovirus, adeno-associated virus, and naked DNA vectors. See, for example, by Anderson et al., U.S. Pat. No. 5,399,346; Mann et al., *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; Dougherty et al., WIPO publication WO 95/07358; and Kuo et al., *Blood* 82:845, 1993. Of particular interest is local infection of the affected tissue, such as local application of the vector to a periodontal pocket, fracture, joint, implant site, or site of prosthetic attachment.

The invention is further illustrated by the following, non-limiting examples.

EXAMPLE 1

An expression plasmid containing all or part of a polynucleotide encoding zvegf3 is constructed via homologous recombination. A fragment of zvegf3 cDNA is isolated by PCR using the polynucleotide sequence of SEQ ID NO: 1 with flanking regions at the 5' and 3' ends corresponding to the vector sequences flanking the zvegf3 insertion point. The primers for PCR each include from 5' to 3' end: 40 bp of flanking sequence from the vector and 17 bp corresponding to the amino and carboxyl termini from the open reading frame of zvegf3.

Ten µl of the 100 µl PCR reaction is run on a 0.8% low-melting-temperature agarose (SeaPlaque GTG®; FMC BioProducts, Rockland, Me.) gel with 1×TBE buffer for analysis. The remaining 90 µl of PCR reaction is precipitated with the addition of 5 µl 1 M NaCl and 250 µl of absolute ethanol. The plasmid pZMP6, which has been cut with SmaI, is used for recombination with the PCR fragment. Plasmid pZMP6 was constructed from pZP9 (deposited at the American Type Culture Collection, 10801 University Boulevard, Manassas, Va. 20110-2209, under Accession No. 98668) with the yeast genetic elements taken from pRS316 (deposited at the American Type Culture Collection, 10801 University Boulevard, Manassas, Va. 20110-2209, under Accession No. 77145), an internal ribosome entry site (IRES) element from poliovirus, and the extracellular domain of CD8 truncated at the C-terminal end of the transmembrane domain. pZMP6 is a mammalian expression vector containing an expression cassette having the cytomegalovirus immediate early promoter, multiple restriction sites for insertion of coding sequences, a stop codon, and a human growth hormone terminator. The plasmid also contains an *E. coli* origin of replication; a mammalian selectable marker expression unit comprising an SV40 promoter, enhancer and origin of replication, a DHFR gene, and the SV40 terminator; as well as the URA3 and CEN-ARS sequences required for selection and replication in *S. cerevisiae*.

One hundred microliters of competent yeast (*S. cerevisiae*) cells are independently combined with 10 µl of the various DNA mixtures from above and transferred to a 0.2-cm electroporation cuvette. The yeast/DNA mixtures are electropulsed using power supply settings of 0.75 kV (5 kV/cm), ∞ ohms, 25 µF. To each cuvette is added 600 µl of 1.2 M sorbitol, and the yeast is plated in two 300-µl aliquots onto two URA-D plates and incubated at 30° C. After about 48 hours, the Ura+ yeast transformants from a single plate are resuspended in 1 ml $H_2O$ and spun briefly to pellet the yeast cells. The cell pellet is resuspended in 1 ml of lysis buffer (2% Triton X-100, 1% SDS, 100 mM NaCl, 10 mM Tris, pH 8.0, 1 mM EDTA). Five hundred microliters of the lysis mixture is added to an Eppendorf tube containing 300 µl acid-washed glass beads and 200 µl phenol-chloroform, vortexed for 1 minute intervals two or three times, and spun for 5 minutes in an Eppendorf centrifuge at maximum speed. Three hundred microliters of the aqueous phase is transferred to a fresh tube, and the DNA is precipitated with 600 µl ethanol (EtOH), followed by centrifugation for 10 minutes at 4° C. The DNA pellet is resuspended in 10 µl $H_2O$.

Transformation of electrocompetent *E. coli* host cells (Electromax DH10B™ cells; obtained from Life Technologies, Inc., Gaithersburg, Md.) is done with 0.5–2 ml yeast DNA prep and 40 ul of cells. The cells are electropulsed at 1.7 kV, 25 µF, and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) is plated in 250-µl aliquots on four LB AMP plates (LB broth (Lennox), 1.8% Bacto™ Agar (Difco), 100 mg/L Ampicillin).

Individual clones harboring the correct expression construct for zvegf3 are identified by restriction digest to verify the presence of the zvegf3 insert and to confirm that the various DNA sequences have been joined correctly to one another. The inserts of positive clones are subjected to sequence analysis. Larger scale plasmid DNA is isolated using a commercially available kit (QIAGEN Plasmid Maxi Kit, Qiagen, Valencia, Calif.) according to manufacturer's instructions. The correct construct is designated pZMP6/zvegf3.

EXAMPLE 2

Full-length zvegf3 protein was produced in BHK cells transfected with pZMP6/zvegf3. BHK 570 cells (ATCC CRL-10314) were plated in 10-cm tissue culture dishes and allowed to grow to approximately 50 to 70% confluence overnight at 37° C., 5% $CO_2$, in DMEM/FBS media (DMEM, Gibco/BRL High Glucose; Life Technologies), 5% fetal bovine serum (Hyclone, Logan, UT), 1 mM L-glutamine (JRH Biosciences, Lenexa, Kans.), 1 mM sodium pyruvate (Life Technologies). The cells were then transfected with pZMP6/zvegf3 by liposome-mediated transfection (using (Lipofectamine™; Life Technologies), in serum free (SF) media (DMEM supplemented with 10 mg/ml transferrin, 5 mg/ml insulin, 2 mg/ml fetuin, 1% L-glutamine and 1% sodium pyruvate). The plasmid was diluted into 15-ml tubes to a total final volume of 640 µl with SF media. 35 µl of the lipid mixture was mixed with 605 µl of SF medium, and the mixture was allowed to incubate approximately 30 minutes at room temperature. Five milliliters of SF media was added to the DNA:lipid mixture. The cells were rinsed once with 5 ml of SF media, aspirated, and the DNA:lipid mixture was added. The cells were incubated at 37° C. for five hours, then 6.4 ml of DMEM/10% FBS, 1% PSN media was added to each plate. The plates were incubated at 37° C. overnight, and the DNA:lipid mixture was replaced with fresh 5% FBS/DMEM media the next day. On day 5 post-transfection, the cells were split into T-162 flasks in selection medium (DMEM+5% FBS, 1% L-Gln, 1% NaPyr, 1 $\mu$M methotrexate). Approximately 10 days post-transfection, two 150-mm culture dishes of methotrexate-resistant colonies from each transfection were trypsinized; and the cells are pooled and plated into a T-162 flask and transferred to large-scale culture.

EXAMPLE 3

Recombinant zvegf3 growth factor domain was produced in cultured mammalian cells. A mammalian cell expression vector for the growth factor domain of zvegf3 was constructed essentially as disclosed in Example 1. The coding sequence for the growth factor domain (residues 235–345 of SEQ ID NO:2), joined to a sequence encoding an optimized t-PA secretory signal sequence (U.S. Pat. No. 5,641,655) was joined to the linearized pZMP11 vector downstream of the CMV promoter. The plasmid pZMP11 is a mammalian expression vector containing an expression cassette having the CMV immediate early promoter, a consensus intron from the variable region of mouse immunoglobulin heavy chain locus, Kozak sequences, multiple restriction sites for insertion of coding sequences, a stop codon, and a human growth hormone terminator. The plasmid also contains an IRES element from poliovirus, the extracellular domain of CD8 truncated at the C-terminal end of the transmembrane domain, an *E. coli* origin of replication, a mammalian selectable marker expression unit having an SV40 promoter, enhancer and origin of replication, a DHFR gene, the SV40 terminator, and the URA3 and CEN-ARS sequences required for selection and replication in *S. cerevisiae*. The resulting vector was designated pZMP11/zv3GF-otPA. BHK 570 cells were transfected with pZMP11/zv3GF-otPA and cultured essentially as disclosed in Example 2.

EXAMPLE 4

Recombinant zvegf3 growth factor domain was produced in BHK 570 cells grown in cell factories. Three 15-liter cultures were harvested, and the media were sterile filtered using a 0.2$\mu$ filter. Expression levels were estimated by western blot analysis of media samples concentrated to 20× using a 5K cut-off membrane and serially diluted by two-fold to 1.25× concentration. Signal intensity was compared to a signal on the same blot from an MBP-zvegf3 fusion protein standard for which the protein concentration had been determined by amino acid analysis. Expression levels were consistently between 0.25 and 0.35 mg/L of media.

Protein was purified from conditioned media by a combination of cation exchange chromatography and hydrophobic interaction chromatography. Culture medium was diluted with 0.1 M acetic acid, pH 3.0, containing 0.3 M NaCl at a ratio of 60%:40%, (medium:acetic acid) to deliver a process stream at 14 mS conductivity and pH 4.0. This stream was delivered to a strong cation exchange resin (Poros® HS; PerSeptive Biosystems, Framingham, Mass.) with a bed volume of 50 ml in a 2-cm diameter column at a flow rate of 20 ml/minute. A 50-ml bed was sufficient to process 45 L of media and capture all of the target protein. Bound protein was eluted, following column washing for 10 column volumes in 10 mM acetic acid with 0.15 M NaCl at pH=4.0, by forming a linear gradient to 2M NaCl in 10 mM acetic acid, pH 4.0. Ten-ml fractions were captured into tubes containing 2 ml 2.0 M Tris, pH 8.0 to neutralize the acidity. Samples from the cation exchange column were analyzed by SDS PAGE with silver staining and western blotting for the presense of zvegf3. The vegf3 growth domain eluted at 0.2–0.5 M NaCl. Protein-containing fractions were pooled. A 25-ml bed of chromatography medium (Toso Haas Ether chromatography medium) in a 2 cm diameter column was equilibrated in 1.8 M $(NH_4)_2SO_4$ in 25 mM Na phosphate buffer at pH 7.4. The pooled protein from the cation exchange step was adjusted to 1.8 M $(NH_4)_2SO_4$ in 25 mM Na phosphate, pH 7.0. This stream was flowed over the column at 10 mil/minute. Once the loading was completed the column was washed for 10 column volumes with the equilibration buffer prior to eluting with a 10 column volume gradient formed between the equilibration buffer and 40 mM boric acid at pH 8.8. The zvegf3 growth factor domain protein eluted fairly early in the gradient between 1.5 and 1.0 M $(NH_4)_2SO_4$. At this point the protein was 40–60% pure with a major contaminent being insulin-like growth factor binding protein 4 (IGFBP4).

Protein from the HIC (Ether) chromatography step was applied to a C4 reverse-phase HPLC column. The zvegf3 growth factor domain protein eluted at 36% acetonitrile. This material still contained approximately 20% (mole/mole) IGFB4.

EXAMPLE 5

Recombinant zvegf3 growth factor domain is purified from cell-conditioned media by a combination of cation exchange chromatography, hydrophobic interaction chromatography, and nickel affinity chromatography. Protein is captured on a strong cation exchange medium and eluted essentially as disclosed in Example 4. The eluted protein is further purified by hydrophobic interaction chromatography on an ether resin (Poros® ET; PerSeptive Biosystems). The partially purified zvegf3 protein is then bound to a nickel chelate resin at pH 7.0–8.0 in 25 mM Na phosphate buffer containing 0.25 M NaCl. The bound protein is eluted with a descending pH gradient down to pH 5.0 or an imidazole gradient. The eluate from the nickel column is adjusted to 1 M $(NH_4)_2SO_4$, 20 mM MES (morphilino ethanesulfonic acid) at pH 6.0 and passed through a phenyl ether hydrophobic interaction chromatography column (Poros® PE, PerSeptive Biosystems) that has been equilibrated in 1 M $(NH_4)_2SO_4$, 20 mM MES, pH 6.0. IGFBP4 and minor contaminants are retained on the column. The pass-through fraction, which contains highly purified zvegf3, is collected. The collected protein is desalted according to conventional methods (e.g., dialysis, ion-exchange chromatography).

EXAMPLE 6

Recombinant zvegf3 was analyzed for mitogenic activity on human aortic smooth muscle cells (HAoSMC; Clonetics Corp., Walkersville, Md.) and human umbilical vein endothelial cells (HUVEC; Clonetics Corp.). HAoSMC and HUVEC were plated at a density of 5,000 cells/well in 96-well culture plates and grown for approximately 24 hours in DMEM containing 10% fetal calf serum at 37° C. Cells were quiesced by incubating them for 24 hours in serum-free DMEM/Ham's F-12 medium containing insulin (5 $\mu$g/ml), transferrin (20 $\mu$g/mil), and selenium (16 pg/ml) (ITS). At the time of the assay, the medium was removed, and test samples were added to the wells in triplicate. Test samples consisted of either conditioned media (CM) from adenovirally-infected HaCaT human keratinocyte cells (Boukamp et al., *J. Cell. Biol.* 106:761–771, 1988) expressing full-length zvegf3, purified growth factor domain expressed in BHK cells, or control media from cells infected with parental adenovirus (Zpar). The CM was concentrated 10-fold using a 15 ml centrifugal filter device with a 10K membrane filter (Ultrafree®; Millipore Corp., Bedford, Mass.), then diluted back to 3× with ITS medium and added to the cells. The control CM was generated from HaCaT cells infected with a parental green fluorescent protein-expressing adenovirus and treated identically to the zvegf3 CM. Purified protein in a buffer containing 0.1% BSA was serially diluted into ITS medium at concentrations of 1 µg/ml to 1 ng/ml and added to the test plate. A control buffer of 0.1% BSA was diluted identically to the highest concentration of zvegf3 protein and added to the plate. For measurement of [$^3$H]thymidine incorporation, 20 µl of a 50 µCi/ml stock in DMEM was added directly to the cells, for a final activity of 1 µCi/well. After another 24 hour incubation, mitogenic activity was assessed by measuring the uptake of [$^3$H]thymidine. Media were removed and cells were incubated with 0.1 ml of trypsin until cells detached. Cells were harvested onto 96-well filter plates using a sample harvester (FilterMate™ harvester; Packard Instrument Co., Meriden, Conn.). The plates were then dried at 65° C. for 15 minutes, sealed after adding 40 µl/well scintillation cocktail (Microscint™ O; Packard Instrument Co.) and counted on a microplate scintillation counter (Topcount®; Packard Instrument Co.).

Results presented in Table 2 demonstrate that zvegf3 CM had approximately 1.5-fold higher mitogenic activity on HAoSM cells over control CM, and purified protein caused a maximal 1.8-fold increase in [$^3$H]thymidine incorporation over the buffer control.

TABLE 2

| Sample | CPM Incorporated | |
|---|---|---|
| | Mean | St. dev. |
| zvegf3 (3 × CM) | 81089 | 8866 |
| Zpar (3 × CM) | 58760 | 2558 |
| zvegf3 GF domain, 1 µg/ml | 63884 | 3281 |
| zvegf3 GF domain, 500 ng/ml | 57484 | 9744 |
| zvegf3 GF domain, 100 ng/ml | 70844 | 10844 |
| zvegf3 GF domain, 50 ng/ml | 61164 | 2813 |
| zvegf3 GF domain, 10 ng/ml | 60676 | 1514 |
| zvegf3 GF domain, 5 ng/ml | 60197 | 2481 |
| zvegf3 GF domain, 1 ng/ml | 49205 | 5208 |
| Buffer control | 39645 | 9793 |
| PDGF 10 ng/ml (maximal response) | 50634 | 4238 |
| Media alone (basal response) | 24220 | 2463 |

Results presented in Table 3 demonstrate that zvegf3 CM had no mitogenic activity on HUVEC compared to the control CM, and purified protein caused a maximal 1.3-fold increase in [$^3$H]thymidine incorporation over the buffer control.

TABLE 3

| Sample | CPM Incorporated | |
|---|---|---|
| | Mean | St. dev. |
| zvegf3 (3 × CM) | 62723 | 10716 |
| Zpar (3 × CM) | 61378 | 1553 |
| zvegf3 VEGF domain, 1 µg/ml | 44901 | 6592 |
| zvegf3 VEGE domain, 500 ng/ml | 41921 | 5330 |
| zvegf3 VEGF domain, 100 ng/ml | 35613 | 5187 |
| zvegf3 VEGF domain, 50 ng/ml | 31107 | 525 |
| zvegf3 VEGF domain, 10 ng/ml | 28505 | 2950 |
| zvegf3 VEGF domain, 5 ng/ml | 29290 | 988 |

TABLE 3-continued

| Sample | CPM Incorporated | |
|---|---|---|
| | Mean | St. dev. |
| zvegf3 VEGF domain, 1 ng/ml | 28586 | 2718 |
| Buffer control | 33461 | 404 |
| VEGF 50 ng/ml (maximal response) | 53225 | 5229 |
| Media alone (basal response) | 22264 | 2814 |

EXAMPLE 7

Recombinant zvegf3 protein was assayed for stimulation of intracellular calcium release as an indicator of receptor binding and activation. Cells were cultured in chambered borosilicate coverglass slides. On the day of assay, cells were incubated for 30 minutes at room temperature in KRW buffer (KrebsRingerWollheim; 140 mM NaCl, 3.6 mM KCl, 0.5 mM NaH$_2$PO$_4$, 0.5 mM MgSO$_4$ 2 mM NaHCO$_3$, 3 mM glucose, 1.5 mM CaCl$_2$, 10 mM HEPES pH 7.4) containing 2 µM fura-2 AM (obtained from Molecular Probes Inc., Eugene, Oreg.), washed twice with KRW buffer, and allowed to sit at room temperature for at least 15 minutes before addition of growth factor or cell-conditioned culture medium (CM) to be tested. Changes in cytosolic calcium were measured by fluorescence ratio imaging (excitation at 340 nm divided by excitation at 380 nm). Digital imaging was carried out using an inverted fluorescent microscope (Nikon TE300) equipped with an oil objective (Nikon 40× Plan Fluor). Images were acquired using a Princeton CCD digital camera and analyzed with Universal Imaging Metafluor software. Data are presented in Table 4.

TABLE 4

| Cell Line | Zvegf3 CM | Control CM | VEGF | PDGF BB |
|---|---|---|---|---|
| aortic ring cells | + | − | − | + |
| pericytes | + | − | − | + |
| aortic smooth muscle cells | + | − | − | + |
| aortic adventitial fibroblasts | + | − | − | + |

EXAMPLE 8

Binding of recombinant zvegf3 to PDGF alpha and beta receptors was measured by mass spectrometry using a surface-enhanced laser desorption and ionization (SELDI) instrument (ProteinChip™, Ciphergen Biosystems, Palo Alto, Calif.). For this experiment an 8-spot, preactivated surface array was used. To this amine-activated chip, protein-A (Zymed Laboratories, Inc., San Francisco, Calif.) was added at a concentration of 1 mg/ml, and the chip was incubated at 4° C. for four hours. After blocking with 1M ethanolamine pH 8.0 and subsequent washes (once in 0.1% Triton X-100 in PBS; once in 100 mM Na Acetate, pH4.5, 0.5 M NaCl; once in 100 mM Tris-HCl, pH8.5, 0.5 M NaCl; once in PBS), IgG Fc-receptor extracellular domain fusion proteins (PDGF alpha receptor, PDGF beta receptor, or unrelated control receptor) were added, and the chip was incubated at 4° C. overnight. After three washes in PBS, 250 µl of zvegf3 (300 ng/ml), PDGF-AA, or PDGF-BB was added, and the chip was incubated overnight at 4° C. The chip was washed twice with 0.05% Triton X100, 100 mM HEPES pH 7.2, then twice with deionized water. The chip was allowed to dry at room temperature before two additions of 0.3 microliters of sinapinic acid (Ciphergen Biosystems) in a 50:50 mixture of acetonitrile and 1% trifluroacetic acid. Ligands that bound receptor were retained on the chip after washing and subsequently detected by mass spectrometry. Assignment of a + or − for binding was made by comparing the PDGF receptor mass spectrometry profile to that of an Fc only control for each ligand. Data are shown in Table 5.

TABLE 5

|  | PDGF AA | PDGF AB | PDGF BB | ZVEGF3 |
| --- | --- | --- | --- | --- |
| PDGFR-alpha/Fc | + | + | + | + |
| PDGFR-beta/Fc | +/− | +/− | + | − |

EXAMPLE 9

Hydroxyethyl cellulose (HEC; dry powder) is reconstituted in 100 mM sodium acetate buffer, pH 6.0 containing 0.2% (w/v) methyl paraben to give a concentration of 1.5% HEC (w/v). The mixture is sterilized by autoclaving at 120° for 20 minutes. Zvegf3 protein is added to a final concentration of 250 µg per gram of gel.

EXAMPLE 10

A 2.5% (w/v) hydroxypropylmethyl cellulose (HPMC) gel is prepared by dissolving powdered HPMC in 100 mM citrate buffer, pH 6.0 containing 0.1% (w/v) methyl paraben. The mixture is sterilized by autoclaving at 120° for 20 minutes. Zvegf3 protein is added to a final concentration of 500 µg per gram of gel.

EXAMPLE 11

Zvegf3 is used to regenerate bone and ligament lost to periodontal disease. Teeth showing 20% to 80% reduction of surrounding jaw bone are scaled, then a full-thickness gingival flap is made by an incision to expose the jaw bone and tooth root. The root is planed to remove bacterial plaque and calculus. Zvegf3 is applied to the periodontal pocket in a 2.5% HPMC gel at a dose of 100 µg per tooth. The gingival flap is then closed and held in place by suturing.

EXAMPLE 12

For regeneration of bone lost to periodontal disease, affected teeth are scaled, and a full-thickness gingival flap is made by incision, exposing the jaw bone and tooth root. The root is planed to remove bacterial plaque and calculus. A solution of zvegf3 in 100 mM sodium acetate buffer, pH 6.0 is added to powdered bone to provide a dosage of 100 µg zvegf3 per tooth. The material is thoroughly mixed and applied to the exposed periodontal pocket. The gingival flap is then closed and held in place by suturing.

EXAMPLE 13

Polylactic acid-polyglycolic acid films (50:50) are solvent cast by dissolving approximately 340 mg of polymer granules (Medisorb Technologies International L.P, Wilmington, Del. or Polysciences, Warrington, Pa.) in 10 ml chloroform at room temperature and allowing the solvent to evaporate completely in a slow air flow hood at room temperature. The films are approximately 10 µm thick. Each is cut into a ca. 80 mm×40 mm sheet, resulting in a remaining polymer mass of about 270–290 mg. A solution of zvegf3 and rabbit serum albumin is dispersed on the films, and the liquid is allowed to evaporate. The films are then rolled around 0.9 mm diameter Kirschner wires (K-wires) to provide implants of 1.5 or 3.0 mm diameter as shown in Table 6 and sterilized using cold ethylene oxide gas.

TABLE 6

| Implant Diameter | Zvegf3 (µg) | Albumin (mg) |
| --- | --- | --- |
| 1.5 mm | 100 | 40 |
| 3.0 mm | 10 | 40 |
| 3.0 mm | 100 | 40 |

EXAMPLE 14

To test zvegf3 in an animal model of bone remodeling, seventy three-month-old female Sprague-Dawley rats are weight-matched and divided into seven groups, with ten animals in each group. The study includes a baseline control group of animals sacrificed at the initiation of the study, a control group administered vehicle only, a PBS-treated control group, and a positive control group administered a compound (non-protein or protein) known to promote bone growth. Three dosage levels of zvegf3 protein are administered to the remaining three groups.

Briefly, zvegf3 protein, positive control compound, PBS, or vehicle alone is administered subcutaneously once per day for 35 days. All animals are injected with calcein nine days and two days before sacrifice (two injections of calcein administered each designated day). Weekly body weights are determined. At the end of the 35-day cycle, the animals are weighed and bled by orbital or cardiac puncture.

Serum calcium, phosphate, osteocalcin, and CBCs are determined. Both leg bones (femur and tibia) and lumbar vertebrae are removed, cleaned of adhering soft tissue, and stored in 70% ethanol for evaluation. The effect of zvegf3 protein on bone remodeling is performed by peripheral quantitative computed tomography (pQCT; Ferretti, *Bone* 17:353S-364S, 1995), dual energy X-ray absorptiometry (DEXA; Laval-Jeantet et al., *Calcif Tissue Intl.* 56:14–18, 1995; Casez et al., *Bone and Mineral* 26:61–68, 1994) and/or histomorphometry.

EXAMPLE 15

Zvegf3 is tested in acute ovariectomized animals (prevention model) using an in vivo dosing assay with an estrogen-treated group as a control. Eighty three-month-old female Sprague-Dawley rats are weight-matched and divided into eight groups, with ten animals in each group. This includes a baseline control group of animals sacrificed at the initiation of the study; three control groups (sham ovariectomized (sham OVX)+vehicle only; ovariectomized (OVX)+vehicle only; PBS-treated OVX); and a control OVX group that is administered estrogen. Three dosage levels of zvegf3 protein are administered to the remaining three groups of OVX animals.

Since ovariectomy (OVX) induces hyperphagia, all OVX animals are pair-fed with sham OVX animals throughout the 35 day study. Briefly, test compound, positive control compound, PBS, or vehicle alone is administered subcutaneously once per day for 35 days. Alternatively, test compound is formulated in implantable pellets that are implanted for 35 days, or may be administered orally, such as by gastric gavage. All animals, including sham OVX/vehicle and OVX/vehicle groups, are injected intraperitoneally with calcein nine days and two days before sacrifice (two injections of calcein administered each designated day, to ensure proper labeling of newly formed bone). Weekly body weights are determined. At the end of the 35-day cycle, the animals' blood and tissues are processed as described above.

EXAMPLE 16

Zvegf3 is tested in chronic OVX animals (treatment model). 80 to 100 six-month-old female, Sprague-Dawley rats are subjected to sham surgery (sham OVX) or ovariectomy (OVX) at time 0, and 10 rats are sacrificed to serve as baseline controls. Body weights are recorded weekly during the experiment. After approximately 6 weeks of bone depletion (42 days), 10 sham OVX and 10 OVX rats are randomly selected for sacrifice as depletion period controls. Of the remaining animals, 10 sham OVX and 10 OVX rats are used as placebo-treated controls. The remaining OVX animals are treated with 3 to 5 doses of zvegf3 protein for a period of 5 weeks (35 days). As a postitive control, a group of OVX rats is treated with an agent such as PTH, a known anabolic agent in this model (Kimmel et al. *Endocrinology* 132:1577–1584, 1993). To determine effects on bone formation, the femurs, tibiae and lumbar vertebrae 1 to 4 are excised and collected.

The proximal left and right tibiae are used for pQCT measurements, cancellous bone mineral density (BMD) (gravimetric determination), and histology, while the midshaft of each tibiae is subjected to cortical BMD or histology. The femurs are prepared for pQCT scanning of the midshaft prior to biomechanical testing. With respect to lumbar vertebrae (LV), LV2 are processed for BMD (pQCT may also be performed); LV3 are prepared for undecalcified bone histology; and LV4 are processed for mechanical testing.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

What is claimed is:

1. A method for promoting proliferation of cells comprising culturing the cells in an effective amount of a dimeric protein comprising a first polypeptide chain disulfide bonded to a second polypeptide chain, each of said chains consisting essentially of residues 235–345 of SEQ ID NO:2, wherein the cells are osteoblasts or osteoblast precursors.

2. The method of claim wherein the cells are bone marrow stem cells.

3. The method of claim 2 wherein the method comprises the additional step of harvesting the cells from a patient prior to the culturing step.

4. The method of claim 1 wherein each of said polypeptide chains consists of residues X-345 of SEQ ID NO:2, wherein X is an integer from 226 to 235, inclusive.

5. The method of claim 1 wherein the cells are osteoblast precursors and wherein at least a portion of the cells differentiate into osteoblasts.

6. The method of claim 5 wherein the method comprises the additional step of harvesting the cells from a patient prior to the culturing step.

7. The method of claim 1 wherein the cells are osteoblasts.

8. The method of claim 7 wherein each of said polypeptide chains consists of residues X-345 of SEQ ID NO:2, wherein X is an integer from 226 to 235, inclusive.

9. A method for promoting differentiation of cells, comprising culturing the cells in an effective amount of a dimeric protein comprising a first polypeptide chain disulfide-bonded to a second polypeptide chain, wherein each of said first and second polypeptide chains consisting essentially of amino acid residues 235–345 of SEQ ID NO:2, and wherein the cells are osteoblast precursors, whereby at least a portion of the cells differentiate into osteoblasts.

10. The method of claim 9, comprising the additional step of harvesting the cells from a patient prior to the culturing step.

11. The method of claim 9 wherein the cells are bone marrow stem cells.

12. The method of claim 11, comprising the additional step of harvesting the cells from a patient prior to the culturing step.

13. The method of claim 9 wherein each of said first and second polypeptides consists of residues X-345 of SEQ ID NO:2, wherein X is an integer from 226 to 235, inclusive.

* * * * *

SEQUENCE LISTING

```
<160> NUMBER OF SEQ ID NOS: 5

<210> SEQ ID NO 1
<211> LENGTH: 1760
<212> TYPE: DNA
<213> ORGANISM: Homo sapiens
<220> FEATURE:
<221> NAME/KEY: CDS
<222> LOCATION: (154)...(1191)

<400> SEQUENCE: 1
attatgtgga aactaccctg cgattctctg ctgccagagc aggctcggcg cttccacccc      60
agtgcagcct tccctggcg gtggtgaaag agactcggga gtcgctgctt ccaaagtgcc      120
cgccgtgagt gagctctcac cccagtcagc caa atg agc ctc ttc ggg ctt ctc      174
                                   Met Ser Leu Phe Gly Leu Leu
                                    1               5 ctg ctg aca tct gcc ctg gcc ggc cag aga cag ggg act cag gcg gaa      222
Leu Leu Thr Ser Ala Leu Ala Gly Gln Arg Gln Gly Thr Gln Ala Glu
         10                  15                  20 tcc aac ctg agt agt aaa ttc cag ttt tcc agc aac aag gaa cag aac      270
Ser Asn Leu Ser Ser Lys Phe Gln Phe Ser Ser Asn Lys Glu Gln Asn
     25                  30                  35 gga gta caa gat cct cag cat gag aga att att act gtg tct act aat      318
Gly Val Gln Asp Pro Gln His Glu Arg Ile Ile Thr Val Ser Thr Asn
 40                  45                  50                  55 gga agt att cac agc cca agg ttt cct cat act tat cca aga aat acg      366
Gly Ser Ile His Ser Pro Arg Phe Pro His Thr Tyr Pro Arg Asn Thr
                 60                  65                  70 gtc ttg gta tgg aga tta gta gca gta gag gaa aat gta tgg ata caa      414
Val Leu Val Trp Arg Leu Val Ala Val Glu Glu Asn Val Trp Ile Gln
             75                  80                  85 ctt acg ttt gat gaa aga ttt ggg ctt gaa gac cca gaa gat gac ata      462
Leu Thr Phe Asp Glu Arg Phe Gly Leu Glu Asp Pro Glu Asp Asp Ile
         90                  95                 100 tgc aag tat gat ttt gta gaa gtt gag gaa ccc agt gat gga act ata      510
Cys Lys Tyr Asp Phe Val Glu Val Glu Glu Pro Ser Asp Gly Thr Ile
    105                 110                 115 tta ggg cgc tgg tgt ggt tct ggt act gta cca gga aaa cag att tct      558
Leu Gly Arg Trp Cys Gly Ser Gly Thr Val Pro Gly Lys Gln Ile Ser
120                 125                 130                 135 aaa gga aat caa att agg ata aga ttt gta tct gat gaa tat ttt cct      606
```

```
Lys Gly Asn Gln Ile Arg Ile Arg Phe Val Ser Asp Glu Tyr Phe Pro
            140                 145                 150 tct gaa cca ggg ttc tgc atc cac tac aac att gtc atg cca caa ttc      654
Ser Glu Pro Gly Phe Cys Ile His Tyr Asn Ile Val Met Pro Gln Phe
            155                 160                 165 aca gaa gct gtg agt cct tca gtg cta ccc cct tca gct ttg cca ctg      702
Thr Glu Ala Val Ser Pro Ser Val Leu Pro Pro Ser Ala Leu Pro Leu
            170                 175                 180 gac ctg ctt aat aat gct ata act gcc ttt agt acc ttg gaa gac ctt      750
Asp Leu Leu Asn Asn Ala Ile Thr Ala Phe Ser Thr Leu Glu Asp Leu
        185                 190                 195 att cga tat ctt gaa cca gag aga tgg cag ttg gac tta gaa gat cta      798
Ile Arg Tyr Leu Glu Pro Glu Arg Trp Gln Leu Asp Leu Glu Asp Leu
200             205                 210                 215 tat agg cca act tgg caa ctt ctt ggc aag gct ttt gtt ttt gga aga      846
Tyr Arg Pro Thr Trp Gln Leu Leu Gly Lys Ala Phe Val Phe Gly Arg
                220                 225                 230 aaa tcc aga gtg gtg gat ctg aac ctt cta aca gag gag gta aga tta      894
Lys Ser Arg Val Val Asp Leu Asn Leu Leu Thr Glu Glu Val Arg Leu
            235                 240                 245 tac agc tgc aca cct cgt aac ttc tca gtg tcc ata agg gaa gaa cta      942
Tyr Ser Cys Thr Pro Arg Asn Phe Ser Val Ser Ile Arg Glu Glu Leu
            250                 255                 260 aag aga acc gat acc att ttc tgg cca ggt tgt ctc ctg gtt aaa cgc      990
Lys Arg Thr Asp Thr Ile Phe Trp Pro Gly Cys Leu Leu Val Lys Arg
            265                 270                 275 tgt ggt ggg aac tgt gcc tgt tgt ctc cac aat tgc aat gaa tgt caa     1038
Cys Gly Gly Asn Cys Ala Cys Cys Leu His Asn Cys Asn Glu Cys Gln
280             285                 290                 295 tgt gtc cca agc aaa gtt act aaa aaa tac cac gag gtc ctt cag ttg     1086
Cys Val Pro Ser Lys Val Thr Lys Lys Tyr His Glu Val Leu Gln Leu
                300                 305                 310 aga cca aag acc ggt gtc agg gga ttg cac aaa tca ctc acc gac gtg     1134
Arg Pro Lys Thr Gly Val Arg Gly Leu His Lys Ser Leu Thr Asp Val
            315                 320                 325 gcc ctg gag cac cat gag gag tgt gac tgt gtg tgc aga ggg agc aca     1182
Ala Leu Glu His His Glu Glu Cys Asp Cys Val Cys Arg Gly Ser Thr
            330                 335                 340 gga gga tag ccgcatcacc accagcagct cttgcccaga gctgtgcagt             1231
Gly Gly *
345 gcagtggctg attctattag agaacgtatg cgttatctcc atccttaatc tcagttgttt   1291 gcttcaagga cctttcatct tcaggattta cagtgcattc tgaaagagga gacatcaaac   1351 agaattagga gttgtgcaac agctcttttg agaggaggcc taaaggacag gagaaaaggt   1411 cttcaatcgt ggaaagaaaa ttaaatgttg tattaaatag atcaccagct agtttcagag   1471 ttaccatgta cgtattccac tagctgggtt ctgtatttca gttctttcga tacggcttag   1531 ggtaatgtca gtacaggaaa aaaactgtgc aagtgagcac ctgattccgt tgccttgctt   1591 aactctaaag ctccatgtcc tgggcctaaa atcgtataaa atctggattt ttttttttt    1651 ttttgctca tattcacata tgtaaaccag aacattctat gtactacaaa cctggttttt    1711 aaaaggaac tatgttgcta tgaattaaac ttgtgtcgtg ctgatagga                1760
```

<210> SEQ ID NO 2
<211> LENGTH: 345
<212> TYPE: PRT
<213> ORGANISM: Homo sapiens

<400> SEQUENCE: 2

| | | | | | | | | | | | | | | |
|---|---|---|---|---|---|---|---|---|---|---|---|---|---|---|
|Met|Ser|Leu|Phe|Gly|Leu|Leu|Leu|Thr|Ser|Ala|Leu|Ala|Gly|Gln|
|1| | | |5| | | |10| | | |15| | |

Arg Gln Gly Thr Gln Ala Glu Ser Asn Leu Ser Ser Lys Phe Gln Phe
            20                  25                  30

Ser Ser Asn Lys Glu Gln Asn Gly Val Gln Asp Pro Gln His Glu Arg
        35                  40                  45

Ile Ile Thr Val Ser Thr Asn Gly Ser Ile His Ser Pro Arg Phe Pro
 50                  55                  60

His Thr Tyr Pro Arg Asn Thr Val Leu Val Trp Arg Leu Val Ala Val
 65                  70                  75                  80

Glu Glu Asn Val Trp Ile Gln Leu Thr Phe Asp Glu Arg Phe Gly Leu
                85                  90                  95

Glu Asp Pro Glu Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
        115                 120                 125

Val Pro Gly Lys Gln Ile Ser Lys Gly Asn Gln Ile Arg Ile Arg Phe
130                 135                 140

Val Ser Asp Glu Tyr Phe Pro Ser Glu Pro Gly Phe Cys Ile His Tyr
145                 150                 155                 160

Asn Ile Val Met Pro Gln Phe Thr Glu Ala Val Ser Pro Ser Val Leu
                165                 170                 175

Pro Pro Ser Ala Leu Pro Leu Asp Leu Leu Asn Asn Ala Ile Thr Ala
            180                 185                 190

Phe Ser Thr Leu Glu Asp Leu Ile Arg Tyr Leu Glu Pro Glu Arg Trp
        195                 200                 205

Gln Leu Asp Leu Glu Asp Leu Tyr Arg Pro Thr Trp Gln Leu Leu Gly
210                 215                 220

Lys Ala Phe Val Phe Gly Arg Lys Ser Arg Val Val Asp Leu Asn Leu
225                 230                 235                 240

Leu Thr Glu Glu Val Arg Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Ser Lys Val Thr Lys Lys
290                 295                 300

Tyr His Glu Val Leu Gln Leu Arg Pro Lys Thr Gly Val Arg Gly Leu
305                 310                 315                 320

His Lys Ser Leu Thr Asp Val Ala Leu Glu His His Glu Glu Cys Asp
                325                 330                 335

Cys Val Cys Arg Gly Ser Thr Gly Gly
            340                 345

<210> SEQ ID NO 3
<211> LENGTH: 3571
<212> TYPE: DNA
<213> ORGANISM: Mus musculus
<220> FEATURE:
<221> NAME/KEY: CDS
<222> LOCATION: (1049)...(2086)

<400> SEQUENCE: 3

-continued

```
gaattcccgg gtcgacccac gcgtccgggc gcccagggga aaggaagctg ggggccgcct      60
ggcggcattc ctcgccgcag tgtgggctcc gtctgccgcg gggcccgcag tgccccctgt     120
ctgcgccagc acctgttggc ccgccagctg gccgcccgcg ccccccgcgc ccccgcgcc     180 cgcccggccg ccagccccgc gccccgcgcg ccgcccgctg ggggaaagtg gagacgggga     240
ggggacaaga gcgatcctcc aggccagcca ggccttccct tagccgcccg tgcttagccg     300
ccacctctcc tcagccctgc gtcctgccct gccttagggc aggcatccga gcgctcgcga     360
ctccgagccg cccaagctct cccggcttcc cgcagcactt cgccggtacc cgagggaact     420
tcggtggcca ccgactgcag caaggaggag gctccgcggt ggatccgggc cagtcccgag     480
tcgtccccgc ggcctctctg cccgcccggg acccgcgcgg cactcgcagg gcacggtccc     540 ctcccccag gtgggggtgg ggcgccgcct gccgccccga tcagcagctt tgtcattgat      600
cccaaggtgc tcgcctcgct gccgacctgg cttccagtct ggcttggcgg gaccccgagt     660
cctcgcctgt gtcctgtccc ccaaactgac aggtgctccc tgcgagtcgc cacgactcat     720
cgccgctccc ccgcgtcccc accccttctt tcctccctcg cctacccca ccccccgcac      780 ttcggcacag ctcaggattt gtttaaacct tgggaaactg gttcaggtcc aggtttttgct    840 ttgatccttt tcaaaaactg gagacacaga agagggctct aggaaaaaact tttggatggg    900 attatgtgga aactaccctg cgattctctg ctgccagagc cggccaggcg cttccaccgc     960
agcgcagcct ttccccggct gggctgagcc ttggagtcgt cgcttcccca gtgcccgccg    1020
cgagtgagcc ctcgccccag tcagccaa atg ctc ctc ctc ggc ctc ctc ctg      1072
                                Met Leu Leu Leu Gly Leu Leu Leu
                                 1               5 ctg aca tct gcc ctg gcc ggc caa aga acg ggg act cgg gct gag tcc     1120
Leu Thr Ser Ala Leu Ala Gly Gln Arg Thr Gly Thr Arg Ala Glu Ser
     10                  15                  20 aac ctg agc agc aag ttg cag ctc tcc agc gac aag gaa cag aac gga     1168
Asn Leu Ser Ser Lys Leu Gln Leu Ser Ser Asp Lys Glu Gln Asn Gly
 25                  30                  35                  40 gtg caa gat ccc cgg cat gag aga gtt gtc act ata tct ggt aat ggg     1216
Val Gln Asp Pro Arg His Glu Arg Val Val Thr Ile Ser Gly Asn Gly
                 45                  50                  55 agc atc cac agc ccg aag ttt cct cat aca tac cca aga aat atg gtg     1264
Ser Ile His Ser Pro Lys Phe Pro His Thr Tyr Pro Arg Asn Met Val
             60                  65                  70 ctg gtg tgg aga tta gtt gca gta gat gaa aat gtg cgg atc cag ctg     1312
Leu Val Trp Arg Leu Val Ala Val Asp Glu Asn Val Arg Ile Gln Leu
         75                  80                  85 aca ttt gat gag aga ttt ggg ctg gaa gat cca gaa gac gat ata tgc     1360
Thr Phe Asp Glu Arg Phe Gly Leu Glu Asp Pro Glu Asp Asp Ile Cys
     90                  95                 100 aag tat gat ttt gta gaa gtt gag gag ccc agt gat gga agt gtt tta     1408
Lys Tyr Asp Phe Val Glu Val Glu Glu Pro Ser Asp Gly Ser Val Leu
105                 110                 115                 120 gga cgc tgg tgt ggt tct ggg act gtg cca gga aag cag act tct aaa     1456
Gly Arg Trp Cys Gly Ser Gly Thr Val Pro Gly Lys Gln Thr Ser Lys
                125                 130                 135 gga aat cat atc agg ata aga ttt gta tct gat gag tat ttt cca tct     1504
Gly Asn His Ile Arg Ile Arg Phe Val Ser Asp Glu Tyr Phe Pro Ser
            140                 145                 150 gaa ccc gga ttc tgc atc cac tac agt att atc atg cca caa gtc aca     1552
Glu Pro Gly Phe Cys Ile His Tyr Ser Ile Ile Met Pro Gln Val Thr
        155                 160                 165 gaa acc acg agt cct tcg gtg ttg ccc cct tca tct ttg tca ttg gac     1600
```

```
Glu Thr Thr Ser Pro Ser Val Leu Pro Pro Ser Ser Leu Ser Leu Asp
    170                 175                 180 ctg ctc aac aat gct gtg act gcc ttc agt acc ttg gaa gag ctg att      1648
Leu Leu Asn Asn Ala Val Thr Ala Phe Ser Thr Leu Glu Glu Leu Ile
185                 190                 195                 200 cgg tac cta gag cca gat cga tgg cag gtg gac ttg gac agc ctc tac      1696
Arg Tyr Leu Glu Pro Asp Arg Trp Gln Val Asp Leu Asp Ser Leu Tyr
                205                 210                 215 aag cca aca tgg cag ctt ttg ggc aag gct ttc ctg tat gga aaa aaa      1744
Lys Pro Thr Trp Gln Leu Leu Gly Lys Ala Phe Leu Tyr Gly Lys Lys
            220                 225                 230 agc aaa gtg gtg aat ctg aat ctc ctc aag gaa gag gta aaa ctc tac      1792
Ser Lys Val Val Asn Leu Asn Leu Leu Lys Glu Glu Val Lys Leu Tyr
        235                 240                 245 agc tgc aca ccc cgg aac ttc tca gtg tcc ata cgg gaa gag cta aag      1840
Ser Cys Thr Pro Arg Asn Phe Ser Val Ser Ile Arg Glu Glu Leu Lys
    250                 255                 260 agg aca gat acc ata ttc tgg cca ggt tgt ctc ctg gtc aag cgc tgt      1888
Arg Thr Asp Thr Ile Phe Trp Pro Gly Cys Leu Leu Val Lys Arg Cys
265                 270                 275                 280 gga gga aat tgt gcc tgt tgt ctc cat aat tgc aat gaa tgt cag tgt      1936
Gly Gly Asn Cys Ala Cys Cys Leu His Asn Cys Asn Glu Cys Gln Cys
                285                 290                 295 gtc cca cgt aaa gtt aca aaa aag tac cat gag gtc ctt cag ttg aga      1984
Val Pro Arg Lys Val Thr Lys Lys Tyr His Glu Val Leu Gln Leu Arg
            300                 305                 310 cca aaa act gga gtc aag gga ttg cat aag tca ctc act gat gtg gct      2032
Pro Lys Thr Gly Val Lys Gly Leu His Lys Ser Leu Thr Asp Val Ala
        315                 320                 325 ctg gaa cac cac gag gaa tgt gac tgt gtg tgt aga gga aac gca gga      2080
Leu Glu His His Glu Glu Cys Asp Cys Val Cys Arg Gly Asn Ala Gly
    330                 335                 340 ggg taa ctgcagcctt cgtagcagca cacgtgagca ctggcattct gtgtaccccc      2136
Gly *
345 acaagcaacc ttcatcccca ccagcgttgg ccgcagggct ctcagctgct gatgctggct      2196 atggtaaaga tcttactcgt ctccaaccaa attctcagtt gtttgcttca atagccttcc      2256 cctgcaggac ttcaagtgtc ttctaaaaga ccagaggcac aagaggagt caatcacaaa       2316 gcactgcctt ctagaggaag cccagacaat ggtcttctga ccacagaaac aaatgaaatg      2376 aatgtagatc gctagcaaac tctggagtga cagcatttct tttccactga cagaatggtg      2436 tagcttagtt gtcttgatat gggcaagtga tgtcagcaca agaaaatggt gaaaacaca       2496 cacttgattg tgaacaatgc agaaatactt ggatttctcc aacctgtttg catagataga      2556 cagatgctct gttttctaca aactcaaagc ttttagagag cagctatgtt aataggaatt      2616 aaatgtgcca tgctgaaagg aaagactgaa gttttcaatg cttggcaact tctccgcaat      2676 ttggaggaaa ggtgcggtca tggtttggag aaagcacacc tgcacagagg agtggccttc      2736 ccttcccttc cctctgaggt ggcttctgtg tttcattgtg tatattttta tattctcctt      2796 ttgacattat aactgttggc ttttctaatc ttgttaaata tttctatttt taccaaaggt      2856 atttaatatt cttttttatg acaacctaga gcaattattt ttagcttgat aatttttttt      2916 tctaaacaaa attgttatag ccagaagaac aaagatgatt gatataaaaa tcttgttgct      2976 ctgacaaaaa catatgtatt tcttccttgt atggtgctag agcttagcgt catctgcatt      3036 tgaaaagatg gaatggggaa gtttttagaa ttggtaggtc gcagggacag tttgataaca      3096
```

-continued

```
actgtactat catcaattcc caattctgtt cttagagcta cgaacagaac agagcttgag    3156
taaatatgga gccattgcta acctacccct ttctatggga aataggagta tagctcagag    3216
aagcacgtcc ccagaaacct cgaccatttc taggcacagt gttctgggct atgctgcgct    3276
gtatggacat atcctattta tttcaatact agggttttat tacctttaaa ctctgctcca    3336
tacacttgta ttaatacatg gtattttta tgtacagaag tatatcattt aaggagttca    3396
cttattatac tctttggcaa ttgcaaagaa aatcaacata atacattgct tgtaaatgct    3456
taatctgtgc ccaagttttg tggtgactat ttgaattaaa atgtattgaa tcatcaaata    3516
aaataatctg gctatttgg ggaaaaaaaa aaaaaaaaa aaaagggcg gccgc          3571
```

<210> SEQ ID NO 4
<211> LENGTH: 345
<212> TYPE: PRT
<213> ORGANISM: Mus musculus

<400> SEQUENCE: 4

```
Met Leu Leu Leu Gly Leu Leu Leu Thr Ser Ala Leu Ala Gly Gln
  1               5                  10                  15

Arg Thr Gly Thr Arg Ala Glu Ser Asn Leu Ser Ser Lys Leu Gln Leu
                 20                  25                  30

Ser Ser Asp Lys Glu Gln Asn Gly Val Gln Asp Pro Arg His Glu Arg
             35                  40                  45

Val Val Thr Ile Ser Gly Asn Gly Ser Ile His Ser Pro Lys Phe Pro
 50                  55                  60

His Thr Tyr Pro Arg Asn Met Val Leu Val Trp Arg Leu Val Ala Val
 65                  70                  75                  80

Asp Glu Asn Val Arg Ile Gln Leu Thr Phe Asp Glu Arg Phe Gly Leu
                 85                  90                  95

Glu Asp Pro Glu Asp Asp Ile Cys Lys Tyr Asp Phe Val Glu Val Glu
            100                 105                 110

Glu Pro Ser Asp Gly Ser Val Leu Gly Arg Trp Cys Gly Ser Gly Thr
        115                 120                 125

Val Pro Gly Lys Gln Thr Ser Lys Gly Asn His Ile Arg Ile Arg Phe
130                 135                 140

Val Ser Asp Glu Tyr Phe Pro Ser Glu Pro Gly Phe Cys Ile His Tyr
145                 150                 155                 160

Ser Ile Ile Met Pro Gln Val Thr Glu Thr Thr Ser Pro Ser Val Leu
                165                 170                 175

Pro Pro Ser Ser Leu Ser Leu Asp Leu Leu Asn Asn Ala Val Thr Ala
            180                 185                 190

Phe Ser Thr Leu Glu Glu Leu Ile Arg Tyr Leu Glu Pro Asp Arg Trp
        195                 200                 205

Gln Val Asp Leu Asp Ser Leu Tyr Lys Pro Thr Trp Gln Leu Leu Gly
    210                 215                 220

Lys Ala Phe Leu Tyr Gly Lys Ser Lys Val Val Asn Leu Asn Leu
225                 230                 235                 240

Leu Lys Glu Glu Val Lys Leu Tyr Ser Cys Thr Pro Arg Asn Phe Ser
                245                 250                 255

Val Ser Ile Arg Glu Glu Leu Lys Arg Thr Asp Thr Ile Phe Trp Pro
            260                 265                 270

Gly Cys Leu Leu Val Lys Arg Cys Gly Gly Asn Cys Ala Cys Cys Leu
        275                 280                 285

His Asn Cys Asn Glu Cys Gln Cys Val Pro Arg Lys Val Thr Lys Lys
```

```
                290                 295                 300
Tyr His Glu Val Leu Gln Leu Arg Pro Lys Thr Gly Val Lys Gly Leu
305                 310                 315                 320

His Lys Ser Leu Thr Asp Val Ala Leu Glu His His Glu Glu Cys Asp
                325                 330                 335

Cys Val Cys Arg Gly Asn Ala Gly Gly
                340                 345

<210> SEQ ID NO 5
<211> LENGTH: 370
<212> TYPE: PRT
<213> ORGANISM: Homo sapiens

<400> SEQUENCE: 5

Met His Arg Leu Ile Phe Val Tyr Thr Leu Ile Cys Ala Asn Phe Cys
1               5                   10                  15

Ser Cys Arg Asp Thr Ser Ala Thr Pro Gln Ser Ala Ser Ile Lys Ala
                20                  25                  30

Leu Arg Asn Ala Asn Leu Arg Arg Asp Glu Ser Asn His Leu Thr Asp
            35                  40                  45

Leu Tyr Arg Arg Asp Glu Thr Ile Gln Val Lys Gly Asn Gly Tyr Val
        50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
        275                 280                 285

Asn Val Val Phe Phe Pro Arg Cys Leu Leu Val Gln Arg Cys Gly Gly
290                 295                 300

Asn Cys Gly Cys Gly Thr Val Asn Trp Arg Ser Cys Thr Cys Asn Ser
305                 310                 315                 320
```

```
                                            -continued
Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
                340                 345                 350

Gln Leu Asp His His Glu Arg Cys Asp Cys Ile Cys Ser Ser Arg Pro
            355                 360                 365

Pro Arg
    370
```